United States Patent [19]

Hara et al.

[11] 4,169,150
[45] Sep. 25, 1979

[54] BENZODIAZEPINE DERIVATIVES AND PHARMACEUTICAL COMPOSITIONS CONTAINING SAID DERIVATIVES

[75] Inventors: Takeshi Hara, Hachioji; Yasutaka Kayama; Kazuhiko Itoh, both of Hino; Toshiro Mori, Hachioji; Hitoshi Fujimori, Hino; Tamiko Sunami, Musashino; Yoshinobu Hashimoto, Fujisawa; Sachio Ishimoto, Tokyo, all of Japan

[73] Assignee: Teijin Limited, Japan

[21] Appl. No.: 737,985

[22] Filed: Nov. 2, 1976

[30] Foreign Application Priority Data

| Nov. 12, 1975 | [JP] | Japan | 50-135203 |
| Nov. 14, 1975 | [JP] | Japan | 50-136365 |
| Dec. 24, 1975 | [JP] | Japan | 50-153350 |
| Jan. 14, 1976 | [JP] | Japan | 51-2755 |
| Jul. 20, 1976 | [JP] | Japan | 51-85572 |
| Jul. 20, 1976 | [JP] | Japan | 51-85573 |
| Sep. 3, 1976 | [JP] | Japan | 51-104921 |
| Sep. 7, 1976 | [JP] | Japan | 51-106222 |

[51] Int. Cl.² .................... A61K 31/55; C07D 487/04
[52] U.S. Cl. .................. 424/274; 260/326.47; 260/326.5 SF; 260/326.5 J; 260/326.5 FM; 260/347.3; 260/556 AR; 260/557 R; 260/558 R; 260/561 R; 260/326.5 B; 260/326.9; 544/372; 548/253; 548/217; 548/236; 548/180; 548/200; 548/262; 260/245.7; 260/326 R; 260/326 A; 260/326 C; 260/326 N; 260/326.14 R; 260/326.35; 260/326.36; 260/326.37
[58] Field of Search .......... 260/326.85, 326.9, 326.5 B; 424/274

[56] References Cited

U.S. PATENT DOCUMENTS

| 3,642,820 | 2/1972 | Hester | 260/326.9 |
| 3,917,627 | 11/1975 | Hester et al. | 260/239 BD |
| 3,987,052 | 10/1976 | Hester | 260/308 R |

OTHER PUBLICATIONS

Garcia et al., J. Org. Chem., vol. 33, pp. 1359-1363, (1968).

*Primary Examiner*—Alton D. Rollins
*Attorney, Agent, or Firm*—Wenderoth, Lind & Ponack

[57] ABSTRACT

Novel 4H-pyrrolo[1,2-a][1,4]benzodiazepine derivatives of the formula

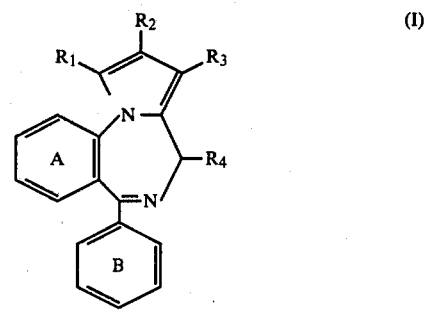

(I)

wherein at least one of $R_1$, $R_2$ and $R_3$ represent lower alkyl and the remainder hydrogen, $R_4$ represents hydrogen or lower alkyl, ring A optionally contains at least one substituent selected from halogen, nitro and trifluoromethyl, and ring B optionally contains at least one substituent selected from halogen, nitro, trifluoromethyl, lower alkyl and lower alkoxy; and novel intermediates thereof expressed by the formula

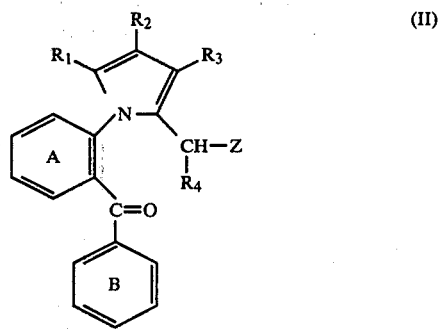

(II)

wherein Z represents protected amino. Compounds of formula (I) are prepared by subjecting compounds of formula (II) to protective group-elimination and cyclization. The compounds of formula (I) and acid addition salts thereof have useful anti-anxietic, sedative, anticonvulsant, muscle relaxant and hypnotic, and their toxicity is low.

26 Claims, No Drawings

BENZODIAZEPINE DERIVATIVES AND PHARMACEUTICAL COMPOSITIONS CONTAINING SAID DERIVATIVES

This invention relates to novel benzodiazepine derivatives, and more specifically, to novel 4H-pyrrolo[1,2-a][1,4]benzodiazepine derivatives containing at least one lower alkyl substituent on the pyrrole ring or acid addition salts thereof, novel intermediates thereof, processes for preparing these derivatives and intermediates, and to use of these benzodiazepine derivatives as medicines.

8-Chloro-6-phenyl-4H-pyrrolo[1,2-a][1,4]benzodiazepine of the following formula

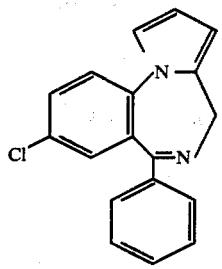

has been reported as a 4H-pyrrolo[1,2-a][1,4]benzodiazepine derivative [Edward E. Garcia et al., J. Org. Chem., 33 (4), 1359–1363 (1968)]. The 4H-pyrrolo[1,2-a][1,4]benzodiazepine derivative of the above formula in which the pyrrole ring is unsubstituted does not substantially show those pharmacological actions which are common to many other known benzodiazepines, such as anti-anxietic, sedative, hypnotic, muscle relaxant, and/or anti-convulsant actions. The process for preparing the compound of the above formula disclosed in the above literature reference is complicated, and the yield of the final product is not satisfactory.

In has now been found surprisingly that novel 4H-pyrrolo[1,2-a][1,4]benzodiazepine derivatives containing at least one lower alkyl substituent on the pyrrole ring can be easily produced by subjecting N-protected derivatives of the correspondingly substituted 2-(2-aminomethylpyrrol-1-yl)benzophenones to elimination of the amino-protecting group and to cyclization, and that the 4H-pyrrolo[1,2-a][1,4]benzodiazepine derivatives so prepared have low toxicity and superior pharmacological actions such as anti-anxietic, anti-spastic, anti-convulsant, muscle relaxant, hypnotic, and taming actions.

It is an object of this invention therefore to provide novel 4H-pyrrolo[1,2-a][1,4]benzodiazepine derivatives containing at least one lower alkyl group on the pyrrole ring.

Another object of this invention is to provide a process for producing the above novel 4H-pyrrolo[1,2-a][1,4]benzodiazepine derivatives simply and effectively.

Still another object of this invention is to provide novel intermediates useful for the manufacture of the above novel 4H-pyrrolo[1,2-a][1,4]benzodiazepine derivatives.

Still another object of this invention is to provide a process for preparing the above intermediates.

A further object of this invention is to provide a pharmaceutical composition containing the novel 4H-pyrrolo[1,2-a][1,4]benzodiazepine derivative as an active ingredient.

A still further object of this invention is to provide a method for treating anxiety, insomnia, muscular spasms, convulsant diseases, and acute and chronic alcoholism, etc.

Other objects and advantages of this invention will become apparent from the following description.

According to this invention, there is firstly provided a compound of the general formula

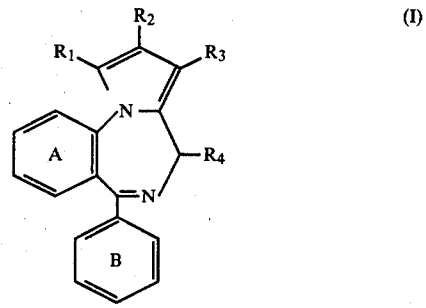

wherein $R_1$, $R_2$ and $R_3$ are identical to, or different from, each other, at least one of them represents a lower alkyl group, and the remainder a hydrogen atom; $R_4$ represents a hydrogen atom or a lower alkyl group; ring A optionally contains at least one substituent selected from the group consisting of halogen atoms, a nitro group and a trifluoromethyl group; and ring B optionally contains at least one substituent selected from the group consisting of halogen atoms, a nitro group, a trifluoromethyl group, lower alkyl groups and lower alkoxy groups;

or its acid addition salts.

In the present specification and appended claims, the term "lower alkyl" means a straight-chain or branched-chain saturated aliphatic hydrocarbon containing 1 to 6 carbon atoms, preferably 1 to 3 carbon atoms, and includes, for example, methyl, ethyl, n- or iso-propyl, n-, iso-, sec- or tert-butyl, and n-, iso-, sec- or neo-pentyl. The term "halogen atoms" means fluorine, chlorine, bromine and iodine atoms. The term "lower alkoxy" means a straight-chain or branched-chain saturated aliphatic hydrocarbonoxy group containing 1 to 6 carbon atoms, preferably 1 to 3 carbon atoms, and includes, for example, methoxy, ethoxy, n- or iso-propoxy, n-, iso-, sec- or tert-butoxy, and n-, iso-, sec- or neo-pentoxy.

In the above formula (I), $R_1$, $R_2$ and $R_3$ on the pyrrole ring are identical to, or different from, each other, and represent a hydrogen atom, or a lower alkyl group, preferably an alkyl group containing 1 to 3 carbon atoms, particularly a methyl or ethyl group, with the proviso that $R_1$, $R_2$ and $R_3$ do not represent hydrogen atoms at the same time. In other words, at least one and up to three lower alkyl groups should be present on the pyrrole ring.

$R_4$ as a substituent at the 4-position represents not only a hydrogen atom, but also a lower alkyl group. Generally, however, it is preferably a hydrogen atom.

The benzene ring A may be unsubstituted, but advantageously, substituted by at least one group selected from the group consisting of halogen atoms, a nitro group and a trifluoromethyl group. These substituents may be present at any desired positions (the 7-, 8-, 9-, and/or 10- positions) on ring A. The number of the substituents is not limited to one, but may be at least two. Where there are two or more substituents, they may be different from each other, preferably, only one substituent is present when ring A is to be substituted. In addition, it is preferably at the 8-position. Of the above substituents, chlorine, bromine and iodine atoms, a trifluoromethyl group and a nitro group are especially preferred.

The benzene ring B may be unsubstituted, or substituted by at least one group selected from the group consisting of halogen atoms, a nitro group; a trifluoromethyl group, lower alkyl groups and lower alkoxy groups. When there are substituents, they can be present at any desired positions on benzene ring B. The number of the substituents is not limited to one, but may be 2 to 5, preferably up to 2. When there are two or more substituents, they may be different from each other. Examples of suitable substituents are halogen atoms especially fluorine, chlorine, and bromine, a trifluoromethyl group, alkyl groups containing 1 to 3 carbon atoms, and alkoxy groups containing 1 to 3 carbon atoms. The halogen atoms are particularly preferred.

Preferred species of compounds corresponding to formula (I) are those in which $R_1$, $R_2$ and $R_3$ are identical to, or different from, each other, at least one of them represents an alkyl group containing 1 to 3 carbon atoms, and the remainder a hydrogen atom, $R_4$ represents a hydrogen atom, ring A optionally contains 1 substituent, and ring B optionally contains up to 2 substituents. Namely, they are compounds of the following formula

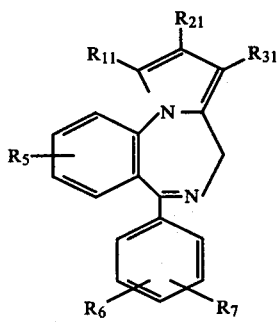

(I-a)

wherein $R_{11}$, $R_{21}$ and $R_{31}$ are identical to, or different from, each other, at least one of them represents an alkyl group containing 1 to 3 carbon atoms and the remainder a hydrogen atom; $R_5$ represents a halogen atom, a nitro group or a trifluoromethyl group; and $R_6$ and $R_7$, independently from each other, represent a hydrogen atom, a halogen atom, a trifluoromethyl group, an alkyl group containing 1 to 3 carbon atoms, or an alkoxy group containing 1 to 3 carbon atoms, and acid addition salts thereof.

More preferred species within formulae (I) and (I-a) above are compounds of the following formula

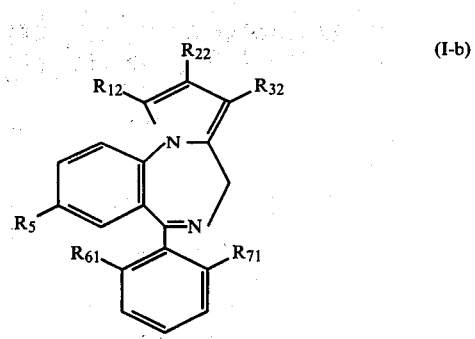

(I-b)

wherein $R_{12}$, $R_{22}$ and $R_{32}$ are identical to, or different from, each other, and at least one of them represents a methyl or ethyl group and the remainder a hydrogen atom; $R_5$ represents a halogen atom, a nitro group or a trifluoromethyl group; and $R_{61}$ and $R_{71}$, independently from each other, represent a hydrogen atom or halogen atom, and acid addition salts thereof.

Some examples of the compounds of formulae (I-a) and (I-b) provided by this invention are listed below.

8-Chloro-1-methyl-6-phenyl-4H-pyrrolo[1,2-a][1,4]benzodiazepine;

8-chloro-6-(2-chlorophenyl)-1-methyl-4H-pyrrolo[1,2-a][1,4]benzodiazepine;

8-chloro-6-(2-fluorophenyl)-1-methyl-4H-pyrrolo[1,2-a][1,4]benzodiazepine;

1-methyl-8-nitro-6-phenyl-4H-pyrrolo[1,2-a][1,4]benzodiazepine;

1-methyl-6-phenyl-8-trifluoromethyl-4H-pyrrolo-[1,2-a][1,4]benzodiazepine;

8-bromo-6-(2-chlorophenyl)-1,2-dimethyl-4H-pyrrolo[1,2-a][1,4]benzodiazepine;

8-chloro-1,2-dimethyl-6-phenyl-4H-pyrrolo[1,2-a][1,4]benzodiazepine;

8-chloro-6-(2-chlorophenyl)-1,2-dimethyl-4H-pyrrolo[1,2-a][1,4]benzodiazepine 8-chloro-1,2-dimethyl-6-(2-fluorophenyl)-4H-pyrrolo[1,2-a][1,4]benzodiazepine;

1,2-dimethyl-8-fluoro-6-(4-methoxyphenyl)-4H-pyrrolo[1,2-a][1,4]benzodiazepine;

6-(2-chlorophenyl)-1,2-dimethyl-8-nitro-4H-pyrrolo-[1,2-a][1,4]benzodiazepine;

1,2-dimethyl-6-(2,4-dimethylphenyl)-8-trifluoromethyl-4H-pyrrolo[1,2-a][1,4]benzodiazepine;

8-chloro-6-(2-chlorophenyl)-2-ethyl-1-methyl-4H-pyrrolo[1,2-a][1,4]benzodiazepine;

8-chloro-2-ethyl-6-(2-fluorophenyl)-1-methyl-4H-pyrrolo[1,2-a][1,4]benzodiazepine;

8-chloro-6-[2,6-difluorophenyl)-2-ethyl-1-methyl-4H-pyrrolo[1,2-a][1,4]benzodiazepine;

2-ethyl-6-(2-fluorophenyl)-1-methyl-8-nitro-4H-pyrrolo[1,2-a][1,4]benzodiazepine;

6-(2-chlorophenyl)-2-ethyl-1-methyl-8-trifluoromethyl-4H-pyrrolo[1,2-a][1,4]benzodiazepine;

8-chloro-2-ethyl-6-phenyl-4H-pyrrolo[1,2-a][1,4]benzodiazepine;

8-chloro-6-(2-chlorophenyl)-2-ethyl-4H-pyrrolo[1,2-a][1,4]benzodiazepine;

8-chloro-2-ethyl-6-(2-fluorophenyl)-4H-pyrrolo-[1,2-a][1,4]benzodiazepine;

8-chloro-6-(2,6-difluorophenyl)-2-ethyl-4H-pyrrolo[1,2-a][1,4]benzodiazepine;

8-chloro-6-(2-chlorophenyl)-2,3-dimethyl-4H-pyrrolo[1,2-a][1,4]benzodiazepine;

8-chloro-2,3-dimethyl-6-(2-fluorophenyl)-4H-pyr-
rolo[1,2-a][1,4]benzodiazepine;
6-(2-chlorophenyl)-2-ethyl-8-nitro-4H-pyrrolo[1,2-
a][1,4]benzodiazepine;
2-ethyl-6-phenyl-8-trifluorophenyl-4H-pyrrolo[1,2-
a][1,4]benzodiazepine;
8-bromo-1,3-dimethyl-6-(2-fluorophenyl)-4H-pyr-
rolo[1,2-a][1,4]benzodiazepine;
8-chloro-6-(2-chlorophenyl)-1,3-dimethyl-4H-pyr-
rolo[1,2-a][1,4]benzodiazepine;
8-chloro-1,3-dimethyl-6-(2-fluorophenyl)-4H-pyr-
rolo[1,2-a][1,4]benzodiazepine;
8-chloro-6-(2,6-difluorophenyl)-1,3-dimethyl-4H-pyr-
rolo[1,2-a][1,4]benzodiazepine;
6-(2-chlorophenyl)-1,3-dimethyl-8-nitro-4H-pyr-
rolo[1,2-a][1,4]benzodiazepine;
1,3-dimethyl-6-(2,4-dimethylphenyl)-8-trifluoromethyl-
4H-pyrrolo[1,2-a][1,4]benzodiazepine,
1,3-dimethyl-8-fluoro-6-(2-fluorophenyl)-4H-pyr-
rolo[1,2-a][1,4]benzodiazepine;
8-chloro-3-ethyl-1-methyl-6-phenyl-4H-pyrrolo[1,2-
a][1,4]-benzodiazepine;
8-chloro-6-(2-chlorophenyl)-3-ethyl-1-methyl-4H-pyr-
rolo[1,2-a][1,4]benzodiazepine;
8-chloro-3-ethyl-6-(2-fluorophenyl)-1-methyl-4H-pyr-
rolo[1,2-a][1,4]benzodiazepine;
8-chloro-6-(2,6-difluorophenyl)-3-ethyl-1-methyl-4H-
pyrrolo[1,2-a][1,4]benzodiazepine;
8-chloro-3-ethyl-1-methyl-6-(3-methylphenyl)-4H-pyr-
rolo[1,2-a][1,4]benzodiazepine;
8-bromo-6-(2-chlorophenyl)-3-methyl-4H-pyrrolo[1,2-
a][1,4]benzodiazepine;
8-chloro-6-(2-chlorophenyl)-3-methyl-4H-pyrrolo[1,2-
a][1,4]benzodiazepine;
8-chloro-6-(2-fluorophenyl)-3-methyl-4H-pyrrolo[1,2-
a][1,4]benzodiazepine;
8-chloro-6-(2,6-difluorophenyl)-3-methyl-4H-pyr-
rolo[1,2-a][1,4]benzodiazepine;
6-(2-chlorophenyl)-3-methyl-8-nitro-4H-pyrrolo[1,2-
a][1,4]benzodiazepine;
3-methyl-6-phenyl-8-trifluoromethyl-4H-pyrrolo[1,2-
a][1,4]benzodiazepine;
8-chloro-3-ethyl-1-methyl-6-phenyl-4H-pyrrolo[1,2-
a][1,4]benzodiazepine;
8-chloro-6-(2-chlorophenyl)-3-ethyl-1-methyl-4H-pyr-
rolo[1,2-a][1,4]benzodiazepine;
8-chloro-3-ethyl-6-(2-fluorophenyl)-1-methyl-4H-pyr-
rolo[1,2-a][1,4]benzodiazepine;
8-chloro-6-(2,6-difluorophenyl)-3-ethyl-1-methyl-4H-
pyrrolo[1,2-a][1,4]benzodiazepine;
6-(2-chlorphenyl)-3-ethyl-1-methyl-8-nitro-4H-pyr-
rolo[1,2-a][1,4]benzodiazepine;
3-ethyl-10methyl-6-phenyl-8-trifluoromethyl-4H-pyr-
rolo[1,2-a][1,4]benzodiazepine;
8-chloro-6-(2-chlorophenyl)-3-ethyl-4H-pyrrolo[1,2-
a][1,4]benzodiazepine;
8-chloro-6-(2,6-difluorophenyl)-3-ethyl-4H-pyr-
rolo[1,2-a][1,4]benzodiazepine;
8-chloro-6-(2-chlorophenyl)-1,2,3-trimethyl-4H-pyr-
rolo[1,2-a][1,4]benzodiazepine;
8-chloro-6-(2,6-difluorophenyl)-1,2,3-trimethyl-4H-pyr-
rolo[1,2-a][1,4]benzodiazepine;
8-chloro-6-(2-chlorophenyl)-3-n-propyl-4H-pyr-
rolo[1,2-a][1,4]benzodiazepine;
8-chloro-6-(2,6-difluorophenyl)-3-n-propyl-4H-pyr-
rolo[1,2-a][1,4]benzodiazepine;
8-chloro-6-(2-chlorophenyl)-2-i-propyl-4H-pyrrolo[1,2-
a][1,4]benzodiazepine; and
8-chloro-6-(2,6-difluorophenyl)-2-iso-propyl-4H-pyr-
rolo[1,2-a][1,4]benzodiazepine.

According to this invention, the compounds of formula (I) and the acid addition salts thereof can be prepared, for example, by subjecting compounds of the general formula

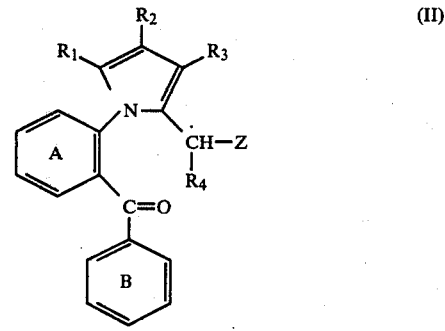

wherein $R_1$, $R_2$, $R_3$, $R_4$, ring A, and ring B are the same as defined above, and Z represents an amino group protected by an amino-protecting group, to elimination of the amino-protecting group and to cyclization, and if desired, converting the product to an acid addition salt.

The amino-protecting group in the "amino group Z protected by an amino-protecting group", referred to herein, may be any hitherto known kind of amino-protecting groups so long as it can be eliminated without substantially adversely effecting the other structural parts of the molecule.

The amino group (Z) protected by an amino-protecting group can be represented by the formula

wherein one of $R_8$ and $R_9$ is a monovalent amino-protecting group and the other is a hydrogen atom, or $R_8$ and $R_9$ together form a divalent amino-protecting group.

Typical examples of the monovalent amino-protecting group are (a) organic carbonyl groups of the formula

wherein $R_{10}$ represents a hydrogen atom, a lower alkyl group, a lower alkenyl group, a lower alkoxy group, a lower alkylthio group, a cycloalkyl group containing 5 to 8 carbon atoms, a cycloalkenyl group containing 5 to 8 carbon atoms, an aryl group containing 6 to 11 carbon atoms, an aralkyl group containing 7 to 13 carbon atoms, an aryloxy group containing 6 to 11 carbon atoms, an aralkoxy group containing 7 to 13 carbon atoms, or a 5- to 10-membered heterocyclic group containing at least one of O, N or S atom, each of the above groups being optionally substituted by a lower alkoxy group, a lower alkylthio group, a cycloalkyloxy group containing 5 to 7 carbon atoms, a cycloalkenyloxy group containing 5 or 6 carbon atoms, a cycloalkylthio group containing 5 or 6 carbon atoms, a cycloalkenylthio group containing 5 or 6 carbon atoms, an aryloxy group containing 6 to 8 carbon atoms, an aralkoxy group containing 7 to 10 carbon atoms, a lower alkyloxycarbonyl group, or a halogen atom;

(b) organic sulfonyl groups of the formula $$R_{11}SO_3—$$

wherein $R_{11}$ represents a substituted or unsubstituted phenyl group; and (c) a triphenylmethyl group.

Specific examples of the organic carbonyl group (a) are formyl, acetyl, propionyl, butyryl, pivaloyl, acryloyl, cyclohexylcarbonyl, cyclopentylacetyl, dihydrophenylacetyl, methoxyacetyl, methylthioacetyl, cyclohexylthioacetyl, cyclohexyloxyacetyl, dihydrophenoxyacetyl, dihydrophenylthioacetyl, benzoyl, tolyl, naphthoyl, α-methylnaphthoyl, phenylacetyl, phenylpropionyl, phenylbutyryl, naphthylacetyl, phenoxyacetyl, benzyloxycarbonyl, naphthoxycarbonyl, phenoxycarbonyl, 2-phenoxypropionyl, 1H (or 2H)-tetrazolylacetyl, thienylacetyl, thienylpropionyl, furylacetyl, piperazinylacetyl, pyrrolidinylacetyl, pyrrolidinylpropionyl, benzothiazolylacetyl, oxazolylacetyl, benzoxazolylacetyl, thiazolylacetyl, pyrazolylacetyl, indolylacetyl, quinolylacetyl, triazolylacetyl, thiadiazolylacetyl, 2-pyridylcarbonyl, methoxycarbonyl, and 2-furyloxycarbonyl.

Examples of the organic sulfonyl groups are benzenesulfonyl, p-toluenesulfonyl, and benzylsulfonyl.

Of these monovalent amino-protecting groups, the organic carbonyl groups, particularly, alkyloxycarbonyl groups, preferably methoxycarbonyl, or ethoxycarbonyl, the cycloalkyloxycarbonyl groups, preferably cyclohexyloxycarbonyl, the aralkyloxycarbonyl groups preferably benzyloxycarbonyl or p-fluorobenzyloxycarbonyl, and the acyl groups (groups resulting from elimination of OH from organic carboxylic acids), preferably acetyl, propionyl, benzoyl, tolyl, or naphthoyl, are advantageously used in the present invention.

Typical examples of the divalent amino-protecting group are organic dicarbonyl groups of the formula $$—OC—R_{12}—CO—$$

wherein $R_{12}$ represents a lower alkylene group, a lower alkenylene group, or a substituted or unsubstituted arylene group. Specific examples of the organic dicarbonyl groups include succinyl, maleoyl, and substituted or unsubstituted phthaloyl.

Especially preferred amino-protecting groups used in this invention are substituted or unsubstituted phthaloyl groups of the formula

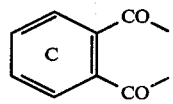

wherein ring C may be substituted. Of these, an unsubstituted phthaloyl group is especially preferred. Substituents on ring C are not particularly restricted, but may be any which does not participate in the reaction. When ring C is substituted, the substituent may be one or more in number and present at any desired positions on ring C. When there are two or more substituents, they may be identical to, or different from, each other, or may be linked to each other to form a ring. Examples of such substituents are lower alkyl groups, lower alkoxy groups, lower alkylthio groups, a methylenedioxy group, and halogen atoms. Examples of phthaloyl groups containing such substituents are 3,6-dimethylphthaloyl, 4,5-dimethylphthaloyl, 3-methoxyphthaloyl, 4-methoxyphthaloyl, 3,4-dimethoxyphthaloyl, 4,5-dimethoxyphthaloyl, 3-methylthiophthaloyl, 3,4-methylenedioxyphthaloyl, 4,5-methylenedioxyphthaloyl, 3-chlorophthaloyl, 4-chlorophthaloyl, 4-bromophthaloyl, 4,5-dichlorophthaloyl, 3,4,5,6-tetrachlorophthaloyl, and 3,4,5,6-tetrabromophthaloyl.

According to the present invention, a compound of formula (II) is subjected to elimination of the amino-protecting group and cyclization. In the present specification and appended claims, the term "elimination of the amino-protecting group and cyclization" denotes the elimination of the amino-protecting group from the amino group (Z) protected by it, and the subsequent cyclization of an intermediate containing a free amino group. However, since the intermediate product resulting after the elimination of the amino-protecting group from the compound of formula (II) contains both a free amino group and a carbonyl group or its reactive derivative, and these groups have a marked tendency to induce a Schiff base-forming reaction and combine with each other, once the amino-protecting group is eliminated from the compound of formula (II), the Schiff base forming reaction takes place in situ under the amino-protecting group elimination conditions, and spontaneously results in the cyclization of the compound of formula (II) without requiring any particular reaction operation. In other words, the elimination of the amino-protecting group from the compound of formula (II) and its cyclization are frequently performed in one step.

Under some reaction conditions for the elimination of the amino-protecting group, the spontaneous in situ cyclization of the compound of formula (II) sometimes does not advantageously proceed even after eliminating the amino-protecting group from it. The spontaneous cyclization is promoted, for example, by heating, and is further promoted by the presence of acidic or basic catalysts.

The amino-protecting group elimination and cyclization in accordance with this invention can be performed by various known methods. In the present invention, however, solvolytic reaction and reduction are advantageously used.

The term "solvolytic reaction", as used in the present specification and appended claims, denotes a reaction wherein a part of the constituent elements of a certain compound is split off by the action of a single solvent or one of compounds which make up a mixed solvent. Such solvolytic reaction includes, for example, hydrolysis, hydrazine decomposition, alcoholysis, aminolysis, and acidlysis. These solvolytic reactions are known per se, and can be performed in accordance with conventional methods. Preferred operation procedures of these methods are shown below.

(1) Hydrolysis

Hydrolysis is carried out preferably by treating the compound of formula (II) with a mineral acid such as hydrochloric acid, hydrobromic acid or sulfuric acid, an aqueous strong organic acid such as trifluoroacetic acid, p-toluenesulfonic acid or phenylphosphoric acid, or an aqueous alkali such as an aqueous solution of sodium hydroxide or an aqueous solution of potassium hydroxide, preferably in a suitable organic solvent (which may be water-miscible or water-immiscible, the former being preferred), for example, an aromatic hydrocarbon such as benzene, toluene or xylene, an alcohol such as methanol or ethanol, an organic carboxylic acid such as acetic acid, propionic acid or trifluoroacetic acid, a halogenated hydrocarbon such as methylene chloride, chloroform or 1,2-dichloroethane, an ether such as diethyl ether, tetrahydrofuran or dioxane, acetonitrile, N,N-dimethylformamide (DMF), or dimethyl sulfoxide (DMSO).

The reaction can be carried out at room temperature to the boiling point of the reaction mixture.

(2) Hydrazine decomposition

Hydrazine decomposition of the compound of formula (II) can be performed using hydrazine or its hydrate.

The amount of hydrazine or its hydrate is preferably at least 1 mole, especially preferably 1 to 30 moles, per mole of the compound of formula (II).

The reaction can be performed by mixing the compound of formula (II) directly with hydrazine or its hydrate without using a solvent. Or it may be carried out using a suitable solvent. Any solvents which do not hamper the reaction can be used for this purpose. Examples are aromatic hydrocarbons, alcohols, ethers, and lower-molecular-weight amides. Readily available solvents are, for example, aromatic hydrocarbons such as benzene or toluene, alcohols such as methanol or ethanol, ethers such as tetrahydrofuran or dioxane, N,N-dimethylformamide, and dimethyl sulxomide. These solvents may be used as a mixture of two or more.

Generally, the reaction is carried out at room temperature to the boiling point of the solvent used. Temperatures near the boiling point of the solvent used are preferred since the cyclization reaction subsequent to the elimination of the amino-protecting group is promoted, and the amino-protecting group eliminating reaction and the cyclization reaction can be achieved in one step.

(3) Alcoholysis

The alcoholysis can be performed almost in the same way as in the hydrolysis mentioned in (1) above except that an alcohol, for example, a lower alkanol such as methanol, ethanol, or n- or iso-propanol, is used instead of the water in the mineral acid, aqueous strong organic acid or aqueous alkali used in the hydrolysis.

(4) Aminolysis

The aminolysis can be performed in substantially the same manner as in the hydrazine decomposition mentioned in (2) above except that an amine is used instead of the hydrazine or its hydrate used in the hydrazine decomposition. Examples of the amine are aliphatic primary amines such as n-butylamine, 2-methoxyethylamine or n-pentylamine; aliphatic secondary amines such as diethylamine, methylpropylamine, or di-n-propylamine; aralkylamines such as benzylamine, phenetylamine, or N-methylbenzylamine; and cyclic amines such as pyrrolidine, piperazine, or piperidine.

(5) Acidlysis

The acidlysis can be performed by treating the compound of formula (II) with a suitable acid at about 0° C. to the boiling point of the reaction mixture. Examples of suitable acids are carboxylic acids such as acetic acid, monochloroacetic acid, dichloroacetic acid, trichloroacetic acid, and trifluoroacetic acid. This treatment may be carried out in an organic solvent of the types examplified above.

With some types of the amino-protecting group, the elimination of the amino-protecting group from the compound of formula (II) and the subsequent cyclization may be effected by reduction. For example, when the amino-protecting group is an aralkyloxycarbonyl group such as benzyloxycarbonyl or p-fluorobenzyloxycarbonyl, the compound may be catalytically hydrogenated with hydrogen at substantially atmospheric pressure in a solvent, for example, the aromatic hydrocarbon, halogenated hydrocarbon, or alcohol mentioned above or an ester such as ethyl acetate in the presence of, for example, palladium-on-charcoal, palladium black, palladium on barium sulfate, platinum oxide, or ruthenium on charcoal. The reduction is usually carried out at room temperature, and the reduction product is already partly cyclized, but a greater part of it remains as an intermediate containing a free amino group, By heating the reduction product to at least 40° C. in the presence or absence of an acidic or basic catalyst after separating the catalyst, the cyclization can be promoted.

When the amino-protecting group is an aralkyloxycarbonyl group such as benzyloxycarbonyl or p-fluorobenzyloxycarbonyl or organic sulfonyl group such as benzylsulfonyl, the reduction of the compound of formula (II) can be performed also with sodium-liquid ammonia.

Which of the procedures for eliminating the amino-protecting group is to be used is determined according to the type of the amino-protecting group present in the compound of formula (II). This determination will be obvious to those skilled in the art.

Furthermore, depending upon the amino-protecting group eliminating means, the compound of formula (II) is not entirely cyclized, but a greater part of it remains as an intermediate having a free amino acid which is expressed by the following formula

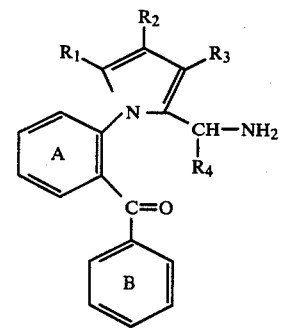

wherein $R_1$, $R_2$, $R_3$, $R_4$, ring A, and ring B are the same as defined hereinabove, or its reactive derivative at the carbonyl group.

In such a case, the compound can be cyclized by heating to a temperature of at least about 40° C., preferably about 60° C. to the boiling point of the reaction mixture, in a solvent of the types mentioned above. This cyclization is promoted by an acid or basic catalyst. The acid catalyst is, for example, hydrogen chloride, hydrogen bromide, sulfuric acid, trifluoroacetic acid, p-toluenesulfonic acid, or phenylphosphoric acid. Examples of the basic catalyst are sodium methoxide, sodium ethoxide, triethylamine, and pyridine. If required, the cyclization may be carried out in the presence of a dehydrating agent such as anhydrous sodium sulfate, anhydrous magnesium sulfate, molecular sieves, calcium chloride, or anhydrous alumina.

The compound of formula (I) so formed can be separated from the reaction mixture and/or purified by conventional procedures, for example, recrystallization, extraction, chromatography, or salt-forming reaction.

The compounds of formula (II) used as starting substances in the above reaction are novel compounds not described in the literature, and form part of the present invention.

In the formula (II), groups $R_1$, $R_2$, $R_3$, $R_4$, and rings A and B have the same meanings as given with regard to formula (I), and group Z is advantageously of the phthalimide type of the formula

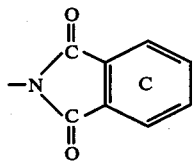

wherein ring C may be substituted by one or more groups which do not participate in the reaction. Substituents on ring C are the same as defined hereinabove.

Preferred species of the compounds included within the formula (II) are compounds expressed by the following formula

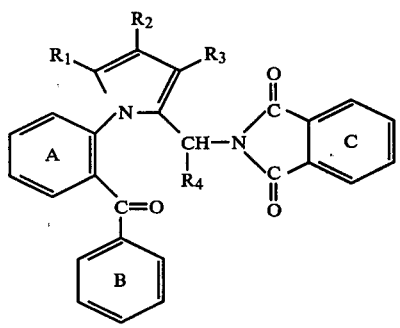

(II-a)

wherein $R_1$, $R_2$, $R_3$, $R_4$ and rings A, B and C are the same as defined hereinabove.

More preferred species of the compounds included within the formula (II-a) are compounds of the formula (II-b)

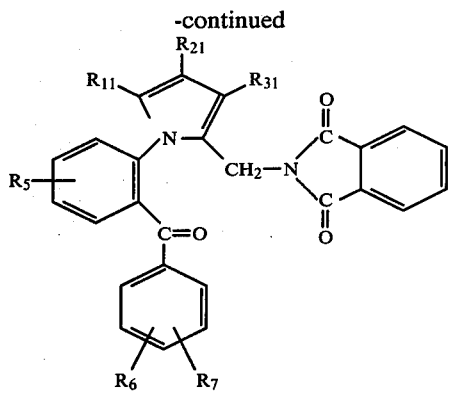

wherein $R_{11}$, $R_{21}$, $R_{31}$, $R_5$, $R_6$ and $R_7$ are the same as defined hereinabove. Of these, those having the following formula

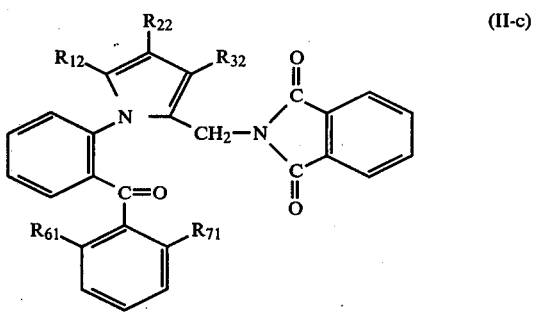

(II-c)

wherein $R_{12}$, $R_{22}$, $R_{32}$, $R_5$, $R_{61}$, and $R_{71}$ are the same as defined hereinabove, are preferred.

Specific examples of the compounds of formula (II) including formulae (II-a), (II-b), and (II-c) used as starting materials in the process of this invention are listed below.

2-(2-Acetamido-5-methylpyrrol-1-yl)-5-chlorobenzophenone,

2′,5-dichloro-2-(2-methyl-5-phthalimidomethylpyrrol-1-yl)benzophenone, 2-(2-benzamidomethyl-5-methylpyrrol-1-yl)-5-chloro-2′-fluorobenzophenone, 2-(2-methyl-5-p-toluenesulfonamidomethylpyrrol-1-yl)-5-nitrobenzophenone, 2-(2-methyl-5-succinimidomethylpyrrol-1-yl)-5-trifluoromethylbenzophenone, 5-bromo-2′-chloro-2-(2,3-dimethyl-5-thienylacetamidomethylpyrrol-1-yl)benzophenone, 5-chloro-2-(2,3-dimethyl-5-phthalimidomethylpyrrol-1-yl)benzophenone, 2′,5-dichloro-2-(2,3-dimethyl-5-thienylacetamidomethylpyrrol-1-yl)benzophenone, 2-(2-benzyloxycarboxamidomethyl-4,5-dimethylpyrrol-1-yl)-5-chloro-2′-fluorobenzophenone, 2-[2,3-dimethyl-5-(3-methylthiophthalimidomethyl)-pyrrol-1-yl]-5-fluoro-4′-methoxybenzophenone, 2-(2-acetamidomethyl-4,5-dimethylpyrrol-1-yl)-2′-chloro-5-nitrobenzophenone, 2-(2-benzamidomethyl-4,5-dimethylpyrrol-1-yl)-2′,4′-dimethyl-5-trifluoromethylbenzophenone, 2′,5-dichloro-2-(3-ethyl-2-methyl-5-phthalimidomethyl-pyrrol-1-yl)benzophenone, 5-chloro-2-(2-cyclohexanecarboxamidomethyl-4-ethyl-5-methylpyrrol-1-yl)-2′-fluorobenzophenone, 2-(2-benzamidomethyl-4-ethyl-5-methylpyrrol-1-yl)-2',6'-difluorobenzophenone,
2-(4-ethyl-2-maleinimidomethyl-5-methylpyrrol-1-yl)-2'-fluoro-5-nitrobenzophenone,
2'-chloro-2-[2-(4-chlorophthalimidomethyl)-4-ethyl-5-methylpyrrol-1-yl]-5-trifluoromethylbenzophenone,
2-(2-benzyloxycarboxamidomethyl-4-ethylpyrrol-1-yl)-5-chlorobenzophenone,
2',5-dichloro-2-(2-ethyl-5-tritylaminomethylpyrrol-1-yl)benzophenone,
5-chloro-2-[2-(3,6-dimethylphthalimidomethyl)-4-ethylpyrrol-1-yl]-2'-fluorobenzophenone,
5-chloro-2',6'-difluoro-2-[4-ethyl-2-(3-methylthiophthalimidomethyl)pyrrol-1-yl]benzophenone,
2',5-dichloro-2-(2,3-dimethyl-5-p-toluenesulfonamidomethylpyrrol-1-yl)benzophene,
5-chloro-2-[2,3-dimethyl-5-(4-methoxyphthalimidomethyl)pyrrol-1-yl]-2'-fluorobenzophenone,
2'-chloro-2-(4-ethyl-2-succinimidomethylpyrrol-1-yl)-5-nitrobenzophenone,
2-(4-ethyl-2-thienylcarboxamidomethylpyrrol-1-yl)-5-trifluoromethylbenzophenone,
5-bromo-2-(2-cyclohexancarboxamidomethyl-3,5-dimethylpyrrol-1-yl)-2'-fluorobenzophenone,
2',5-dichloro-2-(3,5-dimethyl-2-succinimidomethylpyrrol-1-yl)benzophenone,
5-chloro-2-[2-(4-chlorophthalimidomethyl)-3,5-dimethylpyrrol-1-yl]-2'-fluorobenzophenone,
5-chloro-2',6'-difluoro-2-(3,5-dimethyl-2-p-toluenesulfonamidomethylpyrrol-1-yl)benzophenone,
2-(2-benzamidomethyl-3,5-dimethylpyrrol-1-yl)-2'-chloro-5-nitrobenzophenone,
2-(2-acetamidomethyl-3,5-dimethylpyrrol-1-yl)-2',4'-dimethyl-5-trifluoromethylbenzophenone,
2-(3,5-dimethyl-2-phenoxyacetamidomethylpyrrol-1-yl)-2',5-fluorobenzophenone,
5-chloro-2-(4-ethyl-2-methyl-5-phthalimidomethylpyrrol-1-yl)benzophenone,
2',5-dichloro-2-(4-ethyl-2-methyl-5-phthalimidomethylpyrrol-1-yl)benzophenone,
5-chloro-2-(2-cyclohexanecarboxamidomethyl-3-ethyl-5-methylpyrrol-1-yl)-2'-fluorobenzophenone,
2-(2-benzamidomethyl-3-ethyl-5-methylpyrrol-1-yl)-5-chloro-2',6'-difluorobenzophenone,
5-chloro-2-(4-ethyl-2-methyl-5-succinimidomethylpyrrol-1-yl)-3'-methylbenzophenone,
5-bromo-2'-chloro-2-(3-methyl-2-maleinimidomethylpyrrol-1-yl)benzophenone,
2-(2-benzyloxycarboxamidomethyl-3-methylpyrrol-1-yl)-2',5-dichlorobenzophenone,
2-(2-benzyloxycarboxamidomethyl-3-methylpyrrol-1-yl)-5-chloro-2'-fluorobenzophenone,
5-chloro-2-[2-(4-chlorophthalimidomethyl)-3-methylpyrrol-1-yl]-2',6'-difluorobenzophenone,
2-(2-acetamidomethyl-3-methylpyrrol-1-yl)-2'-chloro-5-nitrobenzophenone,
2-(2-benzamidomethyl-3-methylpyrrol-1-yl)-5-trifluoromethylbenzophenone,
5-chloro-2-(3-ethyl-5-methyl-2-phthalimidomethylpyrrol-1-yl)benzophenone,
2',5-dichloro-2-[3-ethyl-5-methyl-2-(4-methoxyphthalimidomethyl)pyrrol-1-yl]benzophenone,
2-(2-acetamidomethyl-3-ethyl-5-methylpyrrol-1-yl)-5-chloro-2'-fluorobenzophenone,
5-chloro-2',6'-difluoro-2-(3-ethyl-5-methyl)-2-thienylacetamidomethylpyrrol-1-yl)benzophenone,
2'-chloro-2-(3-ethyl-5-methyl-2-phenoxyacetamidomethylpyrrol-1-yl)-5-nitrobenzophenone,
2-[3-ethyl-5-methyl-2-(3,6-dimethylphthalimidomethyl)pyrrol-1-yl]-5-trifluoromethylbenzophenone,
2',5-dichloro-2-(3-ethyl-2-phthalimidomethylpyrrol-1-yl)benzophenone,
2-(2-acetamidomethyl-3-ethylpyrrol-1-yl)-5-chloro-2',6'-difluoromethylbenzophenone,
2-(2-benzamidomethyl-3,4,5-trimethylpyrrol-1-yl)-2',5-dichlorobenzophenone,
5-chloro-2',6'-difluoro-2-(2-phthalimidomethyl-3,4,5-trimethylpyrrol-1-yl)benzophenone,
2',5-dichloro-2-(2-phthalimidomethyl-3-n-propylpyrrol-1-yl)benzophenone,
5-chloro-2',6'-difluoro-2-(2-phthalimidomethyl-3-n-propylpyrrol-1-yl)benzophenone,
2',5-dichloro-2-[2-(4-methoxylphthallimidomethyl)-5-n-propylpyrrol-1-yl]benzophenone, and
5-chloro-2',6'-difluoro-2-(2-phthalimidomethyl-4-isopropylpyrrol-1-yl)benzophenone.

According to this invention, the novel compound of formula (II) can be prepared, for example, by reacting a benzophenone derivative of the general formula

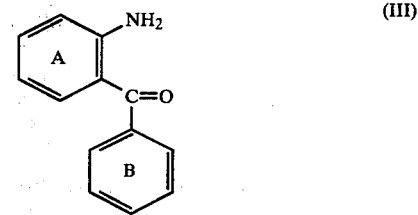

wherein rings A and B are the same as defined above, with an aminodiketone derivative of the general formula

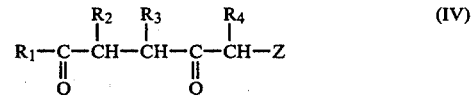

wherein $R_1$, $R_2$, $R_3$, $R_4$ and Z are the same as defined hereinabove, or a tetrahydrofurfurylamine derivative of the general formula

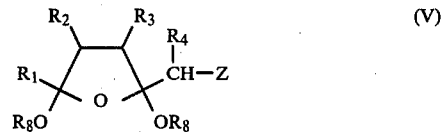

wherein $R_8$ represents a lower alkyl group, and $R_1$, $R_2$, $R_3$, $R_4$ and Z are the same as defined hereinabove.

The reaction of the benzophenone derivative of formula (III) with the aminodiketone derivative of formula (IV) or the tetrahydrofurfuryl amine derivative of formula (V) can be carried out usually in an inert organic solvent. Any inert organic solvents which do not hamper the reaction can be used for this purpose. Examples of the solvents include aromatic hydrocarbons such as benzene, toluene, xylene or chlorobenzene, alcohols such as methanol, ethanol, n-propanol, iso-propanol or ethylene glycol monomethyl ether, ketones such as acetone, diethyl ketone or methyl ethyl ketone, carboxylic acids such as acetic acid or propionic acid, ethers such as tetrahydrofuran, dioxane or ethylene glycol dimethyl ether, esters such as ethyl acetate, halogenated hydrocarbons such as chloroform, methylene chloride, carbon tetrachloride, or 1,2-dichloroethane, acetonitrile, N,N-dimethylformamide, and dimethyl sulfoxide. These solvents can be used either alone or in admixture of two or more.

The proportion of the aminodiketone derivatives of formula (IV) or the tetrahydrofurfurylamine derivative of formula (V) to the benzophenone derivative of formula (III) is not particularly limited, but can be varied over a wide range according, for example, to the types of the compounds of formulae (III), (IV), and (V), and the reaction conditions. Generally, the compounds of formula (IV) or (V) is used in an amount of at least 0.7 mole, preferably 0.8 to 3 moles, more preferably 1 to 2 moles, per mole of the benzophenone derivative of formula (III).

The reaction temperature is neither critical, but can be varied over a wide range according, for example, to the types and proportions of the reactants used, and the solvent. The reaction may proceed well even at room temperature or below, but advantageously, it can be carried out at an elevated temperature. Generally, the reaction can be carried out at 0° C. to the reflux temperature of the reaction mixture, preferably from room temperature to 120° C.

The present reaction is promoted by the use of an acid catalyst to shorten the reaction time and/or to increase the yield of the desired compound of formula (II). Typical examples of the catalyst that can be used for this purpose are listed below.

(a) Organic sulfonic acids

Substituted or unsubstituted aliphatic sulfonic acids such as methanesulfonic acid, trifluoromethanesulfonic acid, ethanesulfonic acid, propanesulfonic acid or d-10-camphorsulfonic acid; substituted or unsubstituted aromatic sulfonic acids such as benzenesulfonic acid, p-toluenesulfonic acid, α-naphthalenesulfonic acid or 4-bromo-1-naphthalenesulfonic acid; and sulfonic acid-type ion exchange resins.

(b) Organic phosphoric acids

Mono- or di-aryl- or mono- or di-alkyl-phosphoric acids such as phenylphosphoric acid, diphenylphosphoric acid, or diethylphosphoric acid.

(c) Mineral acids

Ortho-phosphoric acid, meta-phosphoric acid, polyphosphoric acid, pyrophosphoric acid, and sulfuric acid.

(d) Carboxylic acids

Acetic acid, monochloroacetic acid, dichloroacetic acid, trichloroacetic acid, and trifluoroacetic acid.

(e) Lewis acids

Boron trifluoride, aluminum chloride, stannous chloride, stannic chloride, and zinc chloride.

These catalysts can be used either alone or in admixture of at least two. Of the above-exemplified catalysts, p-toluenesulfonic acid, trichloroacetic acid, phenylphosphoric acid, and sulfuric acid are especially preferred.

The amount of the catalyst used can be varied over a wide range according to its thpe, the types of the reactants, and other reaction conditions, and is usually at least 0.001 mole, preferably 0.01 to 1 mole, per mole of the benzophenone derivative of formula (III).

Where a liquid catalyst is used, it may be used in a great amount to make it serve also as a solvent.

Benzophenone derivatives of formula (III) used as the starting material in the above reaction are generally known, and typical examples are shown as follows:
2-Aminobenzophenone,
2-amino-5-chlorbenzophenone,
2-amino-2′,5-dichlorobenzophenone,
2-amino-4′,5-dichlorobenzophenone,
2-amino-5-chloro-3′-nitrobenzophenone,
2-amino-5-chloro-2′-fluorobenzophenone,
2-amino-5-chloro-2′,6′-difluorobenzophenone,
2-amino-5-chloro-4′-methoxybenzophenone,
2-amino-5-chloro-4′-methylbenzophenone,
2-amino-2′-chlorobenzophenone,
2-amino-5-bromobenzophenone,
2-amino-5-bromo-2′-chlorobenzophenone,
2-amino-5-bromo-2′-fluorobenzophenone,
2-amino-5-bromo-4′-fluorobenzophenone,
2-amino-2′,5-difluorobenzophenone,
2-amino-5-fluorobenzophenone,
2-amino-5-fluoro-4′-methoxybenzophenone,
2-amino-5-nitrobenzophenone,
2-amino-2′-chloro-5-nitrobenzophenone,
2-amino-2′-fluoro-5-nitrobenzophenone,
2-amino-5-trifluoromethylbenzophenone,
2-amino-2′,4′-dimethyl-5-trifluoromethylbenzophenone,
2-amino-2′-chloro-5-fluorobenzophenone, and
2-amino-2′-fluoro-5-trifluoromethylbenzophenone.

Typical examples of the compounds of formula (IV) or (V) to be reacted with the starting compounds of formula (III) are given below.

Aminodiketone derivatives of formula (IV)

1-Acetamidohexane-2,5-dione,
1-phthalimidohexane-2,5-dione,
1-benzamidohexane-2,5-dione,
1-p-toluenesulfonamidohexane-2,5-dione,
1-succinimidohexane-2,5-dione,
1-thienylacetamidohexane-2,5-dione,
4-methyl-1-phthalimidohexane-2,5-dione,
4-methyl-1-thienylacetamidohexane-2,5-dione,
1-benzyloxycarboxamido-4-methylhexane-2,5-dione,
4-methyl-1-(3-methylthiophthalimido)hexane-2,5-dione,
1-acetamido-4-methylhexane-2,5-dione,
1-benzamido-4-methylhexane-2,5-dione,
4-ethyl-1-phthalimidohexane-2,5-dione,
4-ethyl-1-cyclohexancarboxamidohexane-2,5-dione,
1-benzamido-4-ethylhexane-2,5-dione,
4-ethyl-1-maleinimidohexane-2,5-dione,
1-(3-chlorophthalimido)-4-ethylhexane-2,5-dione,
1-benzyloxycarboxamido-4-ethylhexane-2,5-dione,
2-ethyl-3-tritylaminoacetylpropanal,
3-(3,6-dimethylphthalimido)acetyl-2-ethylpropanal,
2-ethyl-3-(3-methylthiophthalimido)acetylpropanal,
2,3-dimethyl-3-p-toluenesulfonamidoacetylpropanal,
2,3-dimethyl-3-(4-methoxyphthalimido)acetylpropanal,
2-ethyl-3-succinimidoacetylpropanal,
2-ethyl-3-thienylacetamidoacetylpropanal,
1-cyclohexancarboxamido-3-methylhexane-2,5-dione,
3-methyl-1-succinimidohexane-2,5-dione,
1-(3-chlorophthalimido)-3-methylhexane-2,5-dione,
3-methyl-1-p-toluenesulfonamidohexane-2,5-dione, 1-benzamido-3-methylhexane-2,5-dione,
1-acetamido-3-methylhexane-2,5-dione,
3-methyl-1-phenoxyacetamidohexane-2,5-dione,
3-ethyl-1-phthalimidohexane-2,5-dione,
1-cyclohexanecarboxamido-3-ethylhexane-2,5-dione,
1-benzamido-3-ethylhexane-2,5-dione,
3-ethyl-1-succinimidohexane-2,5-dione,
3-maleinimidoacetyl-3-methylpropanal,
3-benzyloxycarboxamidoacetyl-3-methylpropanal,
3-(3-chlorophthalimido)acetyl-3-methylpropanal,
3-acetamidoacetyl-3-methylpropanal,
3-benzamidoacetyl-3-methylpropanal, 2-acetamidomethyl-2,5-dimethoxy-3-methyltetrahydrofuran,
2-acetamidomethyl-2,5-dimethoxy-3-ethyltetrahydrofuran,
2-acetamidomethyl-2,5-dimethoxy-3,5-dimethyltetrahydrofuran, and
2-benzamidomethyl-2,5-diethoxytetrahydrofuran.

The compounds of formulae (IV) and (V) are both novel compounds not heretofore described in the literature. They can be produced by the process schematically shown below.

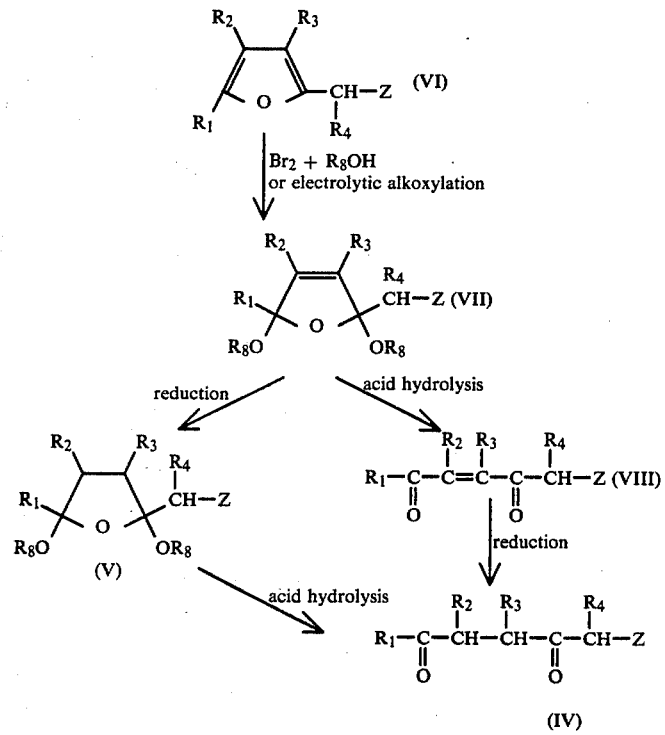

3-ethyl-1-(4-methoxyphthalimido)hexane-2,5-dione,
1-acetamido-3-ethylhexane-2,5-dione,
3-ethyl-1-phenoxyacetylhexane-2,5-dione,
1-(3,6-dimethylphthalimido)-3-ethylhexane-2,5-dione,
1-benzamido-3,4-dimethylhexane-2,5-dione,
3,4-dimethyl-1-phthalimidohexane-2,5-dione,
3-phthalimidoacetyl-3-n-propylpropanal,
3-(4-methoxyphthalimido)acetyl-3-iso-propylpropanal,
3-(3,6-dimethylphthalimido)acetyl-3-iso-propylpropanal.

Tetrahydrofurfurylamine derivatives of formula (V)

2,5-Dimethoxy-2-methyl-5-phthalimidomethyltetrahydrofuran,
2,5-diethoxy-2-methyl-5-phthalimidomethyltetrahydrofuran,
2,5-dimethoxy-3-methyl-5-phthalimidomethyltetrahydrofuran,
2-acetamidomethyl-2,5-dimethoxy-4-methyltetrahydrofuran,
2-acetamidomethyl-2,5-dimethoxy-4-ethyltetrahydrofuran,
2-acetamidomethyl-2,5-dimethoxy-4,5-dimethyltetrahydrofuran,
2-acetamidomethyl-2,5-di-n-propoxy-tetrahydrofuran, In the above formulae, $R_8$ represents a lower alkyl group, and $R_1$, $R_2$, $R_3$, $R_4$ and Z are the same as defined hereinabove.

The conversion of the compound of formula (VI) to the compound of formula (VII) can be achieved by treating the compound of formula (VI) with bromine in the presence of an alcohol ($R_8OH$), or by its electrolytic alkoxylation.

Treatment with bromine in the presence of alcohols can be performed usually in an inert organic solvent, for example, an aromatic hydrocarbon such as benzene or toluene, a halogenated hydrocarbon such as chloroform or methylene chloride, an ether such as diethyl ether, tetrahydrofuran or dioxane, or mixtures of these, using bromine in substantially equimolar amounts to the compound of formula (VI). The alcohol can be used in large excess in order to make it serve also as a solvent. Generally, the amount of the alcohol is at least 2 molar times the amount of the compound of formula (VI).

Preferably, the reaction is carried out generally at low temperatures in the range of −15° to 55° C. Hydrogen bromide which forms as the reaction proceeds is usually neutralized with ammonia gas after the reaction to convert it to ammonium bromide. It may, however, be neutralized with a neutralizing agent added in advance to the reaction vessel. Calcium carbonate and potassium acetate, for example, are suitable as the neutralizing agent.

Electrolytic alkoxylation can be performed, for example, by dissolving 0.05 to 0.5 mole of ammonium bromide and 1 mole of the compound of formula (VI) in an alcohol ($R_8OH$), and passing a current of 2 to 3 A at 4 to 5 V through the solution at $-20°$ to $-5°$ C.

The compound of formula (VIII) obtained above can be converted to a compound of formula (V) by reduction. Reduction is carried out preferably using a catalyst such as Raney nickel, platinum oxide, or palladium. This catalytic reduction can be performed by conventional procedures.

The compound of formula (VII) obtained above can be converted to a compound of formula (VIII) by acid hydrolysis. The acid hydrolysis can be carried out by treating the compound with a mineral acid such as sulfuric acid or hydrochloric acid, preferably in a suitable inert organic solvent, for example, an aromatic hydrocarbon such as benzene, toluene or xylene, a halogenated hydrocarbon such as chloroform, methylene chloride or carbon tetrachloride, an ether such as diethyl ether, tetrahydrofuran or dioxane, or a ketone such as acetone or methyl ethyl ketone. The treating temperature is sufficiently room temperature. But if desired, the treatment may be carried out at an elevated temperature up to the reflux temperature of the reaction mixture.

Reduction of the compound of formula (VIII) can afford the compound of formula (VI). The reduction can be performed by various methods using a wide range of reducing agents. Preferably, there can be used a method of reduction using zinc-acetic acid, or stannous chloride-acetic acid-hydrochloric acid, etc. as reducing agents, and a method of catalytic reduction using palladium black, colloidal palladium, colloidal rhodium, or Raney nickel, etc. as a catalyst. Generally, the reducing reaction is carried out using a solvent. Suitable solvents differ according to the catalyst and reducing agent, and include, for example, alcohols such as methanol or ethanol, carboxylic acid esters such as ethyl acetate, halogenated hydrocarbons such as chloroform or methylene chloride, and carboxylic acids such as formic acid or acetic acid.

Where a catalytic reducing method is used, the reaction rapidly proceeds even at room temperature and about 1 atmosphere as hydrogen pressure, but if desired, it may be carried out at an elevated temperature under pressure in a pressure vessel.

Where a metal and an acid or alcohol, or a metal salt and an acid, are used as the reducing agent, the reducting agent is used in an amount more than that required to generate 2 gram-atoms of nascent state hydrogen per mole of the compound of formula (VIII), and the reaction temperature is from $-20°$ C. to the boiling point of the reaction mixture.

The compound of formula (IV) can be prepared also by the acid hydrolysis of the compound of formula (V). The same acid hydrolysis conditions as described above with regard to the acid hydrolysis of the compound of formula (VII) can be used.

The compound of formula (IV) may be hydrolyzed under stronger conditions using, for example, hydrogen chloride, hydrogen bromide, or sulfuric acid to split off the amino-protecting group to convert it to an acid addition salt of a compound of the following formula

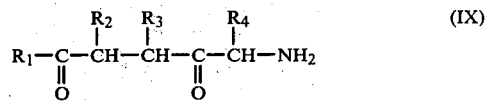

wherein $R_1$, $R_2$, $R_3$ and $R_4$ are the same as defined hereinabove, and then an amino-protecting group different from the one present in the compound of formula (IV) may be introduced into the amino group of the compound of formula (IX) in a customary manner.

According to the present invention, the starting material of formula (II) so prepared is isolated from the reaction mixture and can then be subjected to the elimination of the amino-protecting group and cyclization in accordance with the present invention. One advantage of the process of the invention, however, is that without separating the compound of formula (II) from the reaction mixture, the reaction mixture can directly be subjected to the elimination of the amino-protecting group and cyclization (the so-called "one-vessel process").

Thus, according to a preferred embodiment of the present invention, there is provided a process for preparing compounds of formula (I), which comprises a series of steps of reacting a benzophenone derivative of the general formula

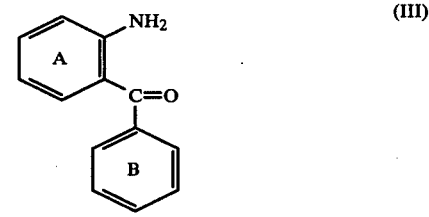

wherein the rings A and B are the same as defined hereinabove,
with an aminodiketone derivative of the general formula

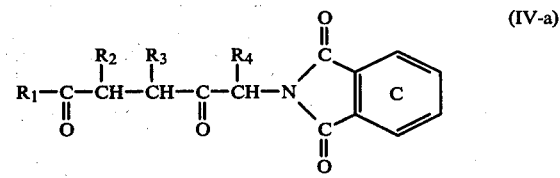

wherein $R_1$, $R_2$, $R_3$, $R_4$ and ring C are the same as defined hereinabove,
or a tetrahydrofurfurylamine derivative of the general formula

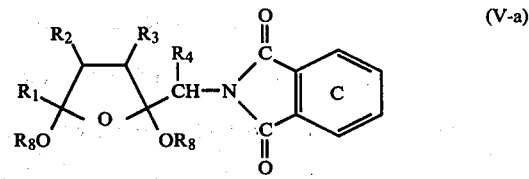

wherein $R_1$, $R_2$, $R_3$, $R_4$, $R_8$ and ring C are the same as defined hereinabove,
to form a compound of the formula

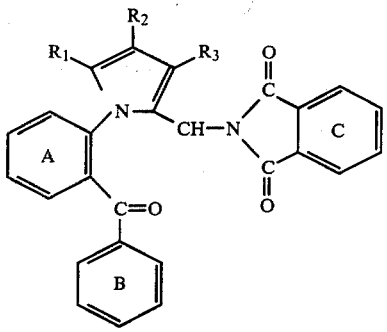 (II-a)

wherein $R_1$, $R_2$, $R_3$, $R_4$ and rings A, B and C are the same as defined hereinabove,
thereafter subjecting the resulting reaction mixture to elimination of the amino-protecting group and cyclization, and if desired, converting the resulting product to an acid addition salt.

According to the process of the invention described above, the benzodiazepine derivative of formula (I) in high purity can be obtained by fewer process steps and in far higher yields than in the known process.

The compounds of formula (I) can be directly used in the applications to be described. Or they can be converted to acid addition salts by treatment with an acid because they contain a basic nitrogen atom in the nucleus.

Conversion to the acid addition salts can be performed by methods known per se. Examples of usable acids are inorganic acids such as hydrogen chloride, hydrogen bromide, sulfuric acid, nitric acid or phosphoric acid, and organic acids such as oxalic acid, succinic acid, malonic acid, tartaric acid, fumaric acid, maleic acid, acetic acid, propionic acid, lactic acid, methanesulfonic acid, or p-toluenesulfonic acid.

Where the compound of formula (I) is obtained in the form of a salt, it can be converted to the desired acid addition salt by first treating it with an alkali to render it free, and then treating the free form with the desired acid.

The compounds of formula (I) and the acid addition salts thereof provided by the present invention exhibit superior central nervous system depressant actions, such as anti-anxietic, taming, sedative, anti-convulsant, anti-spastic, muscle relaxant, and hypnotic, actions, whereas the corresponding compounds having an unsubstituted pyrrole ring do not show any appreciable pharmacological actions. Accordingly, the compounds of formula (I) and the acid addition salts thereof in accordance with this invention are useful as various drugs such as anti-anxietic drugs, sedatives, minor tranquilizers, anti-convulsants, muscle relaxants and hypnotics. In particular, these compounds of the invention are useful as minor tranquilizers because they have strong anti-anxietic and sedative actions and have mild anti-convulsant, muscle relaxant and hypnotic actions.

The compounds of formula (I) and their acid addition salts provided by this invention can therefore be used for prevention, treatment and/or medication of diseases accompanied by anxiety, excitation and convulsion, such as those listed below.
(1) Various kinds of neurosis
(2) Obessive-compulsive behavior
(3) Hysteria
(4) Personality problems
(5) Psychosis with excitation or anxiety
(6) Cerebral palsy with athetosis
(7) Mutiple sclerosis
(8) Hemiplegia
(9) Paraplegia
(10) Pains or anxiety from overriding fractures
(11) Spasms due to tetanus
(12) Stiff-man syndrome
(13) Various kinds of epilepsy, particularly myoclonic seizures, petit mal, and psychomotor seizures
(14) Acute and chronic alcoholism
(15) Neurotic amnesia
(16) Various diseases accompanied, or caused, by tension, hypersensitivity, anxiety, and horror, for example, asthma, angina pectoris, gastric ulcer, and irritable colon
(17) Preanesthetic medication
(18) Anxiety before surgical operation The superior pharmacological actions of the compounds of formula (I) of this invention are demonstrated by the following tests.

In the following tests, the pharmacological actions of the compounds were tested by using six mice (ddY-type male mice) for each dosage level, and $ED_{50}$ values were determined. In the determination of $ED_{50}$ values, the dosages of the test compounds were increased or decreased by a common ratio of 3 as required, and 3 or 4 dosage levels were used. The calculation of the $ED_{50}$ values was made on the basis of the Litchfield-Wilcoxon method [J. Pharmacol. Exp. Therap., 96, 99 (1949)].

Test methods (1) Anti-pentylene tetrazole convulsion activity

Each of test compounds suspended in a 5% gum arabic solution was orally administered to mice. One hour later, pentylene tetrazole in an amount of 125 mg/kg was administered subcutaneously. Then, over the course of 30 minutes, the presence or absence of convulsion in the subjects was examined.

(2) Taming activity

This was determined by a partially modified version of the method of Tedeschi et al. [J. Pharmacol. Exp. Therap., 125, 28 (1959)]. Two mice different in body weight by less than 1 gram were placed in a fighting device, and electroshock (100 V, 3 mA, 0.45 Hz, 0.5 sec) was applied for 3 minutes. Mice which showed more than 7 fighting reactions under these conditions were selected, and orally administered with the test compound. Then, at intervals of 30 minutes, electroshock was applied under the above conditions, and the presence or absence of fighting reaction in the subjects was examined.

(3) Anti-electroshock convulsant activity

The subjects were orally administered with the test compound. One hour later, electroshock (30 mA, 200 Hz, 1 msec) was applied for 0.2 second through both ears, and the presence or absence of tonic extensor convulsion was examined.

(4) Potentiation of thiopental hypnosis

The subjects were orally administered with the test compound. One hour later, sodium thiopental in an amount of 50 mg/kg was administered intraperitoneally. The dosage which prolonged the sleeping time (the period of loss of righting reflex) to two times that in the case of a group administered only with sodium thiopental was determined.

(5) Muscle relaxant activity

Mice were placed on a wooden plate having a smooth surface and being inclined at an angle of 70°, and those which could stay on the initially placed positions for more than 30 seconds were selected. The selected subjects were orally administered with the test compound, and placed on the inclined plate. Examination was made as to whether the mice slipped down within 30 seconds.

(6) Motor incoordinating activity

Mice which could stay for more than 3 minutes on a rotating rod having a diameter of 3.0 cm and rotating at a speed of 5.5 rpm. The subjects were orally administered with the test compound, and then at intervals of 30 minutes, they were placed on the rotating rod. Examination was made as to whether they slipped down within 3 minutes.

The results of these tests are tabulated below. The test compounds used were of the following formula.

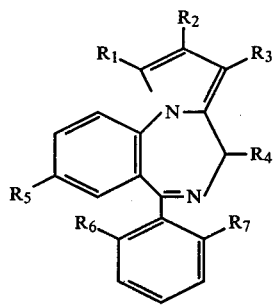

The compounds of formula (I) in accordance with the present invention have a great advantage of having lower toxicity than the conventional benzodiazepine drugs, as is demonstrated by the following experiment.

Test procedure

A test compound was suspended in a 5% solution of gum arabic, and the suspension was administered to a group of 2 to 4 male ddY-type mice in a dose of 1000, 2000, and 3000 mg/kg, respectively. The conditions of the subjects were observed over a period of one week after administration, and the acute toxicity was examined.

It was found that Compounds Nos. 9 and 11 did not cause any death to the subjects even in a dosage of 3000 mg/kg. On the other hand, in the same test, Diazepam caused half of the mice to die with a dosage of 1000 mg/kg.

The compounds of formula (I) and the acid addition salts thereof in accordance with the present invention can be used not only for humans, but also for other mammals and poultry.

These compounds of the invention can be formulated into pharmaceutical compositions comprising a pharmaceutically effective amount of at least one of them in a form suitable for oral or parenteral (e.g., subcutaneous, intramuscular, intravenous, or intrarectal) administration. Forms suitable for oral administration are especially preferred.

For oral administration, the compound of formula (I) or its acid addition salt can be formulated into a solid form (e.g., tablets, troches, pills, capsules, powders, granules, dry syrups, or sugar-coated pills), or a liquid form (e.g., syrups, elixirs, or suspensions).

Tablets, troches, pills, powders, granules, and dry syrups can contain, in addition to the active compound of the invention, a binder such as starch, crystalline cellulose, tragacanth gum, gum arabic, polyvinyl pyrrolidone or gelatin, a vehicle such as lactose, or calcium phosphate, a disintegrant such as starch, crystalline cellulose, or calcium carbocymethyl cellulose, or a lusterant such as talc or magnesium stearate. As required, a sweetening such as sucrose or fructose, and a flavor such as peppermint or cherry flavor can also be added. The capsules can be prepared by adding an inert pharmaceutically acceptable diluent such as lactose, starch, crystalline cellulose, talc or magnesium stearate to the active compound and filling the mixture into hard gelatin capsules of a suitable size, or by dissolving or dispersing the active compound in an inert oil such as vegetable oils or light liquid paraffin and optionally a surfactant or a suspending agent, and filling the resulting solution or suspension into soft gelatin capsules.

The pharmaceuticals in solid dosage forms can be coated with various substances. For example, tablets, pills, or granules can be coated with a cellulose derivative such as hydroxypropylcellulose, shellac, sucrose,

| Pharmacological activity of 4H-pyrrolo(1,2-a) (1,4)benzodiazepines ($ED_{50}$, mg/kg PO, in mice) | | | | | | | | | | | | | |
|---|---|---|---|---|---|---|---|---|---|---|---|---|---|
| | Test compound | | | | | | | Anti-convulsion | | Taming fighting mouse | Muscle relaxation inclined screen | Motor incoordination rotating rod | Sedation potentiation of thiopental |
| No. Diazepan | $R_1$ | $R_2$ | $R_3$ | $R_4$ | $R_5$ | $R_6$ | $R_7$ | pentetrazol | maximal electroshock | | | | |
| | | | | | | | | 0.7 | 8.8 | 1.6 | 1.0 | 5.4 | 0.30 |
| Comparison | H | H | H | H | H | H | H | >100 | >100 | 78 | >100 | >100 | 55 |
| " | H | H | H | H | Cl | H | H | 78 | >100 | >100 | >100 | >100 | 44 |
| " | H | H | H | H | Cl | Cl | H | >100 | >100 | >100 | >100 | >100 | 18 |
| 1 | $CH_3$ | H | H | | Cl | Cl | H | 20 | >100 | 11 | >100 | 100 | 2.8 |
| 2 | $CH_3$ | H | H | | Cl | F | H | 36 | >100 | 55 | >100 | >100 | 6.9 |
| 3 | $CH_3$ | $CH_3$ | H | | Cl | F | H | 10 | >100 | 17 | >100 | >100 | 10 |
| 4 | $CH_3$ | $CH_3$ | H | | Cl | Cl | H | 6.5 | >100 | 4.8 | >100 | 40 | 2.6 |
| 5 | $CH_3$ | $CH_3$ | H | | Cl | H | H | 13.5 | >100 | ≧30 | >100 | >100 | 21 |
| 6 | $CH_3$ | $C_2H_5$ | H | | Cl | Cl | H | 3.4 | >30 | 5.5 | 14 | 23.5 | 0.8 |
| 7 | $CH_3$ | $C_2H_5$ | H | | Cl | F | H | 5.5 | >30 | 5.5 | 30 | >100 | 2.2 |
| 8 | $CH_3$ | $C_2H_5$ | H | | Cl | F | F | 11.2 | >30 | 12.5 | 69 | >100 | 1.9 |
| 9 | $CH_3$ | H | $CH_3$ | | Cl | Cl | H | 1.8 | 100 | 1.6 | 8.2 | 15.5 | 0.34 |
| 10 | $CH_3$ | H | $CH_3$ | | Cl | F | H | 5.5 | >100 | 8.8 | 21.5 | >30 | 2.4 |
| 11 | $CH_3$ | H | $CH_3$ | | Cl | F | F | 2.0 | 88 | 1.6 | 10 | 15.5 | 0.7 | calcium carbonate, talc, gelatin etc. in order to improve their forms.

Liquid preparations such as the syrups or elixirs may contain a sweetening agent such as sucrose, a preservative such as ethyl p-hydroxybenzoate, a coloring agent, and a flavor such as an orange or cherry flavor. In the case of syrups, these additional ingredients are dissolved in an aqueous medium, and in the case of elixirs, they are dissolved in an aqueous ethanol medium.

The suspensions are prepared by using an aqueous medium in the presence of a suspending agent such as gum arabic, tragacanth gum or methyl cellulose.

For parenteral adminitration, the compound of formula (I) or its acid addition salt can be prepared into such a form as an injectable or a suppository. In order to produce injectables, the active compound is suspended or dissolved in a medium. For the preparation of a solution, the active compound is dissolved into water for injection. The solution is sterilized by filtration, and then filled into suitable vials or ampoules. Preferably, adjuvants such as a local anaesthetic, an antiseptic or a buffer are dissolved also in the medium. In order to increase stability, the composition is lyophilized after packing into the vial, and then the vial is sealed. In this case, a vial containing water for injection is attached, and before use, the composition is rendered liquid. The suspension for injection is produced by sterilizing the active compound with ethylene oxide, and then suspending it in a medium. Preferably, uniform dispersing of the compound is promoted by adding a surfactant or a wetting agent to the composition.

The suppository is produced by mixing the active compound with a solid which melts at the body temperature, such as cacao fat, or a solid miscible with the body fluids such as polyethylene glycol.

In preferred embodiments of the present invention, dosage units (which mean physically divisible units suitable as unit administration for patients) can be prepared so that the compound of formula (I) or its acid salt is contained in the amounts mentioned below. For example, the active compound may be included in an amount of 1, 2, 5, 10 or 20 mg for tablets, troches, pills, capsules, and suppositories. Powders and granules may contain the active compound in a concentration of 1 or 10%, and injections 0.01 to 3 W/V %.

The drugs in accordance with the present invention may further contain another pharmacologically active compound.

The dosages of the compound of formula (I) or its acid addition salt differ according to the symptom, age and body weight of a patient, the route of administration, the diagnosis of the physician, etc., and cannot be unequivocally determined. Usually, however, the effective dosages for adults are 0.03 to 3 mg/kg body weight/day. The dosages outside this range can of course be used. The above dosages may be applied at a time, or portionwise.

The following Examples further illustrate the present invention. It should be understood that these examples are only illustrative, and do not in any way limit the scope of the present invention.

EXAMPLE 1 [PREPARATION OF COMPOUND (II)]

2-Aminobenzophenone (360 mg, 1.83 millimoles) and 1-phthalimidohexane-2,5-dione (485 mg, 1.87 millimoles) were dissolved in 20 ml of benzene. To the solution was added 300 mg of trichloroacetic acid, and the mixture was heated under reflux for 1 hour. The reaction mixture was cooled to room temperature, and an excess of a 10% aqueous solution of sodium carbonate was added to neutralize the trichloroacetic acid. The layers were separated, and the benzene layer was washed with an aqueous sodium chloride solution, and dried over anhydrous sodium sulfate. The solvent was evaporated under reduced pressure. The residue was chromatographed on silica gel with benzene-ethyl acetate (19:1) as an eluant to afford 705 mg of light yellow crystals in 92% yield. Recrystallization from methylene chloride-n-hexane afforded light yellow prisms having melting point 117.5°–118.5° C. The spectral data and the result of the elemental analysis of the product were as follows:

IR (KBr) cm$^{-1}$: 1764, 1711, 1650, 1599, 1451, 1418, 1391, 1354, 1330, 1314, 1290, 1103, 930, 924, 770, 744, 732, 705, 695.

NMR (CDCl$_3$), δ (ppm) from TMS: 1.89 (3H, s, CH$_3$) $v_A$ 4.58 and $v_B$ 4.47 (2H, ABq, J=15.5 Hz, CH$_2$N) $v_A$ 6.07 and $v_B$ 5.72 (2H, ABq, J=3.0 Hz, H on the pyrrole ring) 7.22–7.94 (13H, m, H on the benzene rings)

Anal. Calcd. for C$_{27}$H$_{20}$N$_2$O$_3$: C, 77.13; H, 4.80; N, 6.66; Found: C, 77.55; H, 4.69; N, 6.65.

From these characteristics, the product was determined to be 2-(2-methyl-5-phthalimidomethylpyrrol-1-yl)benzophenone.

EXAMPLE 2 [PREPARATION OF COMPOUND (II)]

2-Amino-5-chlorobenzophenone (860 mg, 3.71 millimoles) and 1-phthalimidohexane-2,5-dione (1.00 g, 3.86 millimoles) were dissolved in 50 ml of benzene, and 520 mg of trichloroacetic acid was added. The mixture was heated under reflux for 2 hours.

The resulting mixture was worked up and chromatographed on silica gel in the same manner as in Example 1 to afford 1.57 g of light yellow crystals in 93% yield. Recrystallization from diethyl ether-n-hexane afforded light yellow needles having melting point 148.5°–149.5° C. The spectral data and the result of elemental analysis of the product were as follows:

IR (KBr) cm$^{-1}$: 1765, 1721, 1652, 1481, 1419, 1391, 1352, 1330, 1312, 1283, 1102, 740, 703, 698.

NMR (CDCl$_3$) δ (ppm) from TMS: 1.89 (3H, s, CH$_3$) $v_A$ 4.57 and $v_B$ 4.39 (2H, ABq, J=15.0 Hz, CH$_2$N) $v_A$ 6.03 and 5.69 (2H, ABq, J=3.0 Hz, H on the pyrrole ring) 7.22–7.84 (12H, m, H on the benzene rings)

Anal. Calcd. for C$_{27}$H$_{19}$ClN$_2$O$_3$: C, 71.29; H, 4.21; N, 6.16 Found: C, 71.27; H, 3.97; N, 6.18

From the above characteristics, the product was determined to be 5-chloro-2-(2-methyl-5-phthalimidomethylpyrrol-1-yl)benzophenone.

EXAMPLES 3 [PREPARATION OF COMPOUND (II)]

2-Amino-2',5-dichlorobenzophenone (500 mg, 1.93 millimoles) and 1-phthalimidohexane-2,5-dione (500 mg, 1.88 millimoles) were dissolved by heating in 20 ml of benzene. Then, 50 mg of p-toluenesulfonic acid was added, and the mixture was heated under reflux for 1.5 hours. The reaction mixture was worked up in the same way as in Example 1, and the solvent was evaporated under reduced pressure. The residue was chromatographed on silica gel with benzene-ethyl acetate (49:1) as an eluant to afford 869 mg of light yellow crystals in 95% yield. Recrystallization from methylene chloride-n-hexane afforded light yellow prisms having melting point 170°–170.5° C. The spectral data and the result of elemental analysis of the product were as follows:

IR (KBr) cm$^{-1}$: 1766, 1720, 1668, 1483, 1417, 1391, 1329, 743.

NMR (CDCl$_3$), δ (ppm) from TMS: 1.84 (3H, s, CH$_3$) ν$_A$ 4.51 and ν$_B$ 4.29 (2H, ABq, J=15.5 Hz, CH$_2$N) ν$_A$ 5.90 and ν$_B$ 5.59 (2H, ABq, J=3.5 Hz, H on the pyrrole ring) 7.09–7.36 (5H, m H on the benzene rings)

7.51–7.79 (6H, m, H on the benzene rings)

Anal. Calcd. for C$_{27}$H$_{18}$Cl$_2$N$_2$O$_3$: C, 66.27; H, 3.71; N, 5.72; Found: C, 66.13; H, 3.67; N, 5.57.

From the above characteristics, the reaction product obtained was determined to be 2′,5-dichloro-2-(2-methyl-5-phthalimidomethylpyrrol-1-yl)benzophenone.

EXAMPLE 4 [PREPARATION OF COMPOUND (II)]

2-Amino-5-chloro-2′-fluorobenzophenone (267 mg, 1.07 millimoles) and 1-phthalimidohexane-2,5-dione (290 mg, 1.12 millimoles) were dissolved in 5 ml of benzene, and 30 mg of p-toluenesulfonic acid was added. The mixture was heated under reflux for 1 hour. The reaction mixture was worked up and chromatographed on silica gel in the same was as in Example 3 to afford 443 mg of light yellow crystals in 88% yield. Recrystallization from methylene chloride-n-hexane afforded light yellow prisms having melting point 184°–185° C. The spectral data and the result of elemental analysis of the product were as follows:

IR (KBr) cm$^{-1}$: 1767, 1722, 1661, 1610, 1481, 1416, 1391, 1350, 1327, 1292, 1099, 766, 742.

NMR (CDCl$_3$), δ (ppm) from TMS: 1.87 (3H, s, CH$_3$) ν$_A$ 4.61 and ν$_B$ 4.36 (2H, ABq, J=15.0 Hz, CH$_2$N) ν$_A$ 5.95 and ν$_B$ 5.62 (2H, ABq, J=3.5 Hz, H on the pyrrole ring) 6.88–7.84 (11H, m H on the benzene rings)

Anal. Calcd. for C$_{27}$H$_{18}$ClFN$_2$O$_3$: C, 68.58; H, 3.84; N, 5.92; Found: C, 68.36; H, 3.44; N, 5.85.

From the above characteristics, the product was determined to be 5-chloro-2′-fluoro-2-(2-methyl-5-phthalimidomethylpyrrol-1-yl)benzophenone.

EXAMPLE 5 [PREPARATION OF COMPOUND (II)]

2-Amino-5-nitrobenzene (100 mg, 4.13 millimoles) and 1-phthalimidohexane-2,5-dione (110 mg, 4.24 mg) were dissolved in 5 ml of benzene by heating, and 20 mg of p-toluenesulfonic acid was added. The mixture was heated under reflux for 2.5 hours. The reaction mixture was worked up and chromatographed on silica gel in the same way as in Examples 3 to afford 113 mg of light yellow crystals in 59% yield. Recrystallization from methylene chloride-n-hexane afforded light yellow prisms having melting point 174°–175° C. The spectral data and the result of elemental analysis of the product were as follows:

IR (KBr) cm$^{-1}$: 1764, 1712, 1667, 1609, 1522, 1481, 1417, 1382, 1343, 1302, 1275, 1102, 865, 739, 707, 691.

NMR (CDCl$_3$), δ (ppm) from TMS: 1.91 (3H, s, CH$_3$) ν$_A$ 4.58 and ν$_B$ 4.36 (2H, ABq, J=15.0 Hz, CH$_2$N) ν$_A$ 6.12 and ν$_B$ 5.73 (2H, ABq, J=3.0 Hz, H on the pyrrole ring) 7.28–7.79 (10H, m, H on the benzene rings) 8.41 (2H, m, H on the benzene rings)

Anal. Calcd. for C$_{27}$H$_{19}$N$_3$O$_5$: C, 69.67; H, 4.12; N, 9.03; Found: C, 69.55; H, 3.88; N, 8.76.

From the above characteristics, the product was determined to be 2-(2-methyl-5-phthalimidomethyl-pyrrol-1-yl)-5-nitrobenzophenone.

EXAMPLE 6 [PREPARATION OF COMPOUND (II)]

2-Amino-5-chlorobenzophenone (100 mg, 0.44 millimole) and 4-methyl-1-phthalimidohexane-2,5-dione (120 mg, 0.44 millimole) were dissolved by heating in 5 ml of benzene and 20 mg of p-toluenesulfonic acid was added. The mixture was heated under reflux for 2 hours. The reaction mixture was cooled to room temperature, 20 ml of benzene was added to dissolve the precipitated crystals, and the p-toluenesulfonic acid was neutralized with a saturated aqueous sodium bicarbonate solution. The layers were separated, and the layer was washed with water and an aqueous solution of sodium chloride and dried over anhydrous sodium sulfate. The solvent was evaporated under reduced pressure, and the residue was chromatographed on silica gel with benzene-ethyl acetate (19:1) as an eluant to afford 185 mg of yellow crystals in 92% yield. Recrystallization from methylene chloride-n-hexane afforded light yellow prisms having melting point 160°–160.5° C. The spectral data and the result of elemental analysis of the product were as follows:

IR (KBr) cm$^{-1}$: 1770, 1718, 1660, 1600, 1484, 1426, 1391.

NMR (CDCl$_3$) δ (ppm) from TMS: 1.79 (6H, s, CH$_3$) ν$_A$ 4.58 and ν$_B$ 4.39 (2H, ABq, J=15.0 Hz, CH$_2$N) 5.92 (1H, s, H on the pyrrole ring)

7.27–7.82 (12H, m, H on the benzene rings)

Anal. Calcd. for C$_{28}$H$_{21}$ClN$_2$O$_3$: C, 71.72; H, 4.51; N, 5.97; Found: C, 71.64; H, 4.57; N, 6.06.

From the above characteristics, the product was determined to be 5-chloro-2-(2,3-dimethyl-5-phthalimidomethylpyrrol-1-yl)benzophenone.

EXAMPLES 7 [PREPARATION OF COMPOUND (II)]

2-Amino-2′,5-dichlorobenzophenone (300 mg, 1.13 millimoles) and 4-methyl-1-phthalimidohexane-2,5-dione (315 mg, 1.15 millimoles) were dissolved in 15 ml of benzene. To the solution was added 30 mg of p-toluenesulfonic acid and the mixture was heated under reflux for 1 hour. The reaction mixture was worked up and chromatographed on silica gel in the same way as in Example 6 to afford 548 mg of yellow crystals in 97% yield. Recrystallization from methylene chloride-n-hexane afforded light yellow prisms having melting point 162°–163° C. The spectral data and the result of elemental analysis of the product were as follows:

IR (KBr) cm$^{-1}$: 1766, 1710, 1670, 1588, 1417, 1393.

NMR (CDCl$_3$), δ (ppm) from TMS: 1.71 (3H, s, CH$_3$) 1.73 (3H, s, CH$_3$) ν$_A$ 4.49 and ν$_B$ 4.28 (2H, ABq, J=16.0 Hz, CH$_2$N) 5.74 (1H, s, H on the pyrrole ring) 7.06–7.37 (5H, m, H on the benzene rings)

7.54–7.81 (6H, m, H on the benzene rings)

Anal. Calcd. for C$_{28}$H$_{20}$Cl$_2$N$_2$O$_3$: C, 66.81; H, 4.00; N, 5.57; Found: C, 66.74; H, 3.92; N, 5.72.

From the above characteristics, the product was determined to be 2′,5-dichloro-2-(2,3-dimethyl-5-phthalimidomethylpyrrol-1-yl)benzophenone.

EXAMPLE 8 [PREPARATION OF COMPOUND (II)]

In the same way as in Example 7 except that 2-amino-5-chloro-2′-fluorobenzophenone was used instead of 2-amino-2′,5-dichlorobenzopnenone were obtained light yellow crystals having melting point 150°–152° C. in 94% yield. Recrystallization from methylene chloride-n-hexane afforded light yellow prisms having melting point 152°–153° C. The spectral data and the result of elemental analysis of the product were as follows:

IR (KBr) cm$^{-1}$: 1764, 1709, 1662, 1608, 1480, 1417, 1393

NMR (CDCl$_3$) from TMS, δ (ppm): 1.68 (3H, s, CH$_3$) 1.76 (3H, s, CH$_3$) $\nu_A$ 4.57 and $\nu_B$ 4.32 (2H, ABq, J=15.5 Hz, CH$_2$N) 5.76 (1H, s, H on the pyrrole ring) 6.86–7.80 (11H, m, H on the benzene rings)

Anal. Calcd. for C$_{28}$H$_{20}$ClFN$_2$O$_3$: C, 69.07; H, 4.14; N, 5.75; Found: C, 68.83; H, 4.01; N, 5.72.

From the above characteristics, the product was determined be 5-chloro-2'-fluoro-2-(2,3-dimethyl-5-phthalimidomethylpyrrol-1-yl)benzophenone.

Example 9 (Preparation of compound (II))

2-Amino-2',5-dichlorobenzophenone (420 mg, 1.58 millimoles) and 4-ethyl-1-phthalimidohexane-2,5-dione (472 mg, 1.64 millimoles) were dissolved in 20 ml of benzene by heating. To the solution was added 30 mg of p-toluenesulfonic acid, and the mixture was heated under reflux for 4 hours. After cooling, the mixture was diluted with 20 ml of ethyl acetate, washed successively with a saturated aqueous solution of sodium bicarbonate, water and an aqueous solution of sodium chloride, dried over anhydrous sodium sulfate, and concentrated. Addition of 5 ml of methylene chloride to the residue afforded a colorless solid insoluble in methylene chloride. The solid was collected by filtration and identified as phthalimide from its IR and NMR spectra. The portion soluble in methylene chloride was chromatographed on silica gel first with benzene-n-hexane (2:1) and then with benzene to afford 533 mg of yellow crystals having a melting point of 168° to 169.5° C. in a yield of 65%. Recrystallization from methylene chloride-n-hexane afforded light yellow prisms having a melting point of 170° to 171° C. The spectral data and the results of elemental analysis of the resulting product were as follows:

IR (KBr) cm$^{-1}$: 1763, 1708, 1670, 1481, 1417, 1395, 727.

NMR (CDCl$_3$) from TMS, δ (ppm): 0.93 (3H, t, J=7.5 Hz, CH$_2$CH$_3$ 1.73 (3H, s, =C−CH$_2$) 2.09 (2H, q, J=7.5 Hz, CH$_2$CH$_3$) $\nu_A$ 4.48 and $\nu_B$ 4.25 (2H, ABq, J=15.0 Hz, CH$_2$N)

5.76 (1H, H on the pyrrole ring) 7.04–7.33 (6H, m, H on the benzene rings) 7.55–7.78 (5H, m, H on the benzene rings)

Anal. Calcd. for C$_{29}$H$_{22}$Cl$_2$N$_2$O$_3$: C, 67.32; H, 4.29; N, 5.41; Found: C, 67.08; H, 4.21; N, 5.29.

From the above characteristics, the product was determined to be 2',5-dichloro-2-(3-ethyl-2-methyl-5-phthalimidomethylpyrrol-1-yl)benzophenone.

Example 10 [Preparation of compound (II)]

2-Amino-5-chloro-2'-fluorobenzophenone (530 mg, 2.12 millimoles) and 4-ethyl-1-phthalimidohexane-2,5-dione (648 mg) were dissolved by heating in 25 ml of benzene. To the solution was added 15 mg of p-toluenesulfonic acid, and the mixture was heated under reflux for 20 hours. After cooling, the mixture was washed successively with water, a saturated aqueous solution of sodium bicarbonate and an aqueous solution of sodium chloride, and then dried over anhydrous sodium sulfate. The mixture was concentrated at reduced pressure, and the residue was chromatographed on silica gel. By eluting with benzene 222 mg of 2-amino-5-chloro-2'-fluorobenzophenone was recovered, and elution with benzene-ethyl acetate (95:5) afforded 576 mg of yellow crystals in a yield of 54%. Recrystallized from methylene chloride-n-hexane afforded light yellow plate-like crystals having a melting point of 185° to 186° C. The spectral data and the result of elemental analysis of the product were as follows:

IR (KBr) cm$^{-1}$: 1766, 1718, 1660, 1607, 1479, 1381, 1289, 723.

NMR (CDCl$_3$) from TMS, o(ppm): 0.89 (3H, t, J=7.5 Hz, CH$_2$CH$_3$ 1.76 (3H, s, =C−CH$_3$) 2.08 (2H, q, J=7.5 Hz, CH$_2$CH$_3$) $_A$4.56 and $_B$4.30 (2H, ABq, J=15.5 Hz, CH$_2$N) 5.78 (1H, s, H on the pyrrole ring) 6.84–7.82 (11H, m, H on the benzene rings)

Anal. Calcd. for C$_{29}$H$_{22}$ClFN$_2$O$_3$: C, 69.53; H, 4.43; N, 5.59; Found: C, 69.66; H, 4.28; N, 5.75.

From the above characteristics, the resulting product was determined to be 5-chloro-2'-fluoro-2-(3-ethyl-2-methyl-5-phthalimidomethylpyrrol-1-yl)benzophenone.

EXAMPLE 11 [Preparation of compound (II)]

2-Amino-5-chloro-2',6'-difluorobenzophenone (520 mg, 1.94 millimoles) and 4-ethyl-1-phthalimidohexane-2,5-dione (560 mg, 1.95 millimoles) were dissolved in 30 ml of benzene, and 20 mg of p-toluenesulfonic acid was added. The mixture was heated under reflux for 24 hour. After cooling, the mixture was washed with a 10% aqueous solution of sodium carbonate and an aqueous solution of sodium chloride, and then dried over anhydrous sodium sulfate. The solvent was evaporated under reduced pressure, and the residue was chromatographed on silica gel. The column was first eluted with benzene to recover 99 mg of 2-amino-5-chloro-2',6'-difluorobenzophenone in a recovery ratio of 19%. Then, it was eluted with benzene-ethyle acetate (19:1) to afford 808 mg of yellow crystals in a yield of 80%. Recrystallization from methylene chloride-n-hexane afforded light yellow prisms having a melting point of 198° to 190° C. The spectral data and the result of elemental analysis of the product were as follows:

IR (KBr) cm$^{-1}$: 1767, 1719, 1665, 1619, 1467, 1382, 1012, 808, 723.

NMR (CDCl$_3$) from TMS, δ (ppm): 0.94 (3H, t, J=7.5 Hz, CH$_2$CH$_3$) 1.76 (3H, s, =C−CH$_3$) 2.09 (2H, q, J=7.5 Hz, CH$_2$CH$_3$) $\nu_A$ 4.59 and $\nu_B$ 4.29 (2H, ABq, J=15.0 Hz, CH$_2$N) 5.78 (1H, s, H on the pyrrole ring) 6.68–6.84 (2H, m, H on the benzene rings) 7.11–7.51 (2H, m, H on the benzene rings) 7.59–7.80 (6H, m, H on the benzene rings)

Anal. Calcd. for C$_{29}$H$_{21}$ClF$_2$N$_2$O$_3$: C, 67.12; H, 4.08; N, 5.40: Found: C, 67.05; H, 4.06; N, 5.41.

From the above characteristics, the resulting product was determined to be 5-chloro-2',6'-difluoro-2-(3-ethyl-2-methyl-5-phthalimidomethylpyrrol-1-yl)benzophenone.

EXAMPLE 12 [Preparation of compound (II)]

2-Amino-2',5-dichlorobenzophenone (375 mg, 1.41 millimoles) and 3-methyl-1-phthalimidohexane-2,5-dione (366 mg, 1.34 millimoles) were dissolved in 15 ml of benzene, and 30 mg of p-toluenesulfonic acid was added. The mixture was heated under reflux for 3.5 hours. After cooling, 20 ml of benzene was added. The mixture was washed successively with water, a 10% aqueous solution of sodium carbonate, and an aqueous solution of sodium chloride, and then dried over anhydrous sodium sulfate. The solvent was evaporated under reduced pressure, and the concentrate was chromatographed on silica gel. The column was first eluted with benzene to recover 43 mg of 2-amino-2',5-dichlorobenzophenone, and then eluted with benzene-ethyl acetate (19:1) to afford 608 mg of yellow crystals in a yield of 90%. Recrystallization from benzene-n-hexane afforded light yellow needles having a melting point of 168.5° to 169.5° C. The spectral data and the result of elemental analysis of the product were as follows:

IR (KBr) cm$^{-1}$: 1763, 1708, 1661, 1482, 1422, 1397, 1351, 762, 712.

NMR (CDCl$_3$) from TMS, δ (ppm): 1.82 (3H, s, CH$_3$ at the 3-position) 1.90 (3H, s, CH$_3$ at the 1-position) ν$_A$ 4.63 and ν$_B$ 4.12 (2H, ABq, J=15.5 Hz, CH$_2$N) 5.52 (1H, s, H on the pyrrole ring) 7.01–7.78 (11H, m, H on the benzene rings)

Anal. Calcd. for C$_{28}$H$_{20}$Cl$_2$N$_2$O$_3$: C, 66.81; H, 4.00; N, 5.57; Found: C, 66.62; H, 3.67; N, 5.65.

From the above characteristics, the product was determined to be 2',5-dichloro-2-(2,4-dimethyl-5-phthalimidomethylpyrrol-1-yl)benzophenone.

EXAMPLE 13 [Preparation of compound (II)]

2-Amino-5-chloro-2'-fluorobenzophenone (390 mg, 1.56 millimoles) and 3-methyl-1-phthalimidohexane-2,5-dione (406 mg, 1.49 millimoles) were dissolved in 10 ml of benzene, and 25 mg of p-toluenesulfonic acid was added. The mixture was heated under reflux for 5 hours. The reaction mixture was post-treated and chromatographed on silica gel in the same way as in Example 12. The column was first eluted with benzene to recover 57 mg of 2-amino-5-chloro-2'-fluorobenzophenone, and then with benzene-ethyl acetate (19:1) to afford 596 mg of yellow crystals in a yield of 82%. Recrystallization from methylene chloride-n-hexane afforded light yellow prisms having a melting point of 168° to 169.5° C. The spectral data and the results of elemental analysis of the product were as follows:

IR (KBr) cm$^{-1}$: 1764, 1718, 1661, 1482, 1417, 1394, 1353, 1323, 760.

NMR (CDCl$_3$) from TMS δ (ppm) 1.85 (3H, s, CH$_3$ at the 3-position) 1.90 (3H, s, CH$_3$ at the 1-position) ν$_A$ 4.69 and ν$_B$ 4.26 (2H, ABq, J=15.5 Hz, CH$_2$N) 5.45 (1H, s, H on the pyrrole ring) 6.89–7.79 (11H, m. H on the benzene rings)

Analysis Calcd. for C$_{28}$H$_{20}$ClFN$_2$O$_3$: C, 69.07; H, 4.14; N, 5.75; Found: C, 69.00; H, 4.04; N, 5.72.

From the above characteristics, the product was determined to be 5-chloro-2'-fluoro-2-(2,4-dimethyl-5-phthalimidomethylpyrrol-1-yl)benzophenone.

EXAMPLE 14 [Preparation of compound (II)]

2-Amino-5-chloro-2',6'-difluorobenzophenone (410 mg, 1.53 millimoles) and 3-methyl-1-phthalimidohexane-2,5-dione (399 mg, 1.46 millimoles) were dissolved in 15 ml of benzene, and 30 mg of p-toluenesulfonic acid was added. The mixture was heated under reflux for 16.5 hours. After cooling, the mixture was diluted with 30 ml of ethyl acetate, washed with a 10% aqueous solution of sodium carbonate, and an aqueous solution of sodium chloride, and then dried over anhydrous sodium sulfate. The solvent was evaporated under reduced pressure, and the residue was chromatographed on silica gel. The column was first eluted with benzene to recover 55 mg of 2-amino-5-chloro-2',6'-difluorobenzophenone, and then with benzene-ethyl acetate (49:1) to afford 670 mg of yellow crystals. Recrystallization from methylene chloride -n-hexane afforded light yellow pillar-like crystals having a melting point of 187.5° to 188.5° C. The spectral data of the product were as follows:

IR (KBr) cm$^{-1}$: 1763, 1719, 1662, 1618, 1468, 1416, 1394, 1353, 1011, 797.

NMR (CDCl$_3$) from TMS, δ (ppm): 1.85 (3H, s, CH$_3$ at the 3-position) 1.87 (3H, s, CH$_3$ at the 3-position) ν$_A$ 4.73 and ν$_B$ 4.19 (2H, ABq, J=15.5 Hz, CH$_2$N) 5.36 (1H, s, H on the pyrrole ring) 6.68–6.91 (2H, m, H on the benzene rings) 7.19–7.82 (8H, m, H on the benzene rings)

From the above characteristics the product was determined to be 5-chloro-2',6'-difluoro-2-(2,4-dimethyl-5-phtalimidomethylpyrrol-1-yl)benzophenone.

EXAMPLE 15 [Preparation of compound (II)]

2-amino-5-chlorobenzophenone (180 mg, 0.777 millimole) and 2,5-dimethoxy-2-methyl-5-phthalimidomethyltetrahydrofuran (250 mg, 0.918 millimole) were dissolved in 4 ml of benzene, and 20 mg of p-toluenesulfonic acid was added. The mixture was heated under reflux for 2 hours. After cooling, a 10% aqueous solution of sodium carbonate was stirred. The layers were separated, and the benzene layer was washed with an aqueous solution of sodium chloride, dried over anhydrous sodium sulfate, and concentrated at reduced pressure. The residue was chromatographed on silica gel with benzene-ethyl acetate (98:2) an an eluant to afford 308 mg of light yellow crystals in a yield of 87%. Recrystallization from diethyl ether-n-hexane afforded light yellow needles having a melting point of 148.5° to 149.5° C. The IR and NMR spectra of the product were identical with those of the product obtained in Example 2. The product was therefore determined to be 5-chloro-2-(2-methyl-5-phthalimidomethylpyrrol-1-yl)benzophenone.

EXAMPLE 16 [Preparation of compound (II)]

Example 15 was repeated except that 120 mg of trichloroacetic acid was used instead of the p-toluenesulfonic acid in Example 15, thereby to afford 5-chloro-2-(2-methyl-5-phthalimidomethylpyrrol-1-yl)benzophenone.

EXAMPLE 17 [Preparation of compound (II)]

2-Amino-5-chloro-2'-fluorobenzophenone (330 mg, 132 millimoles) and 2,5-dimethoxy-2-methyl-5-phthalimidomethyltetrahydroguran (422 mg, 1.38 millimoles) were dissolved in 5 ml of benzene, and 30 mg of p-toluenesulfonic acid was added. The mixture was heated under reflux for 2 hours. The reaction mixture was post-treated and chromatographed on silica gel in the same way as in Example 51 to afford 553 mg of light yellow crystals in a yield of 89%. Recrystallization from methylene chloride-n-hexane afforded light yellow prisms having a melting point of 184° to 185° C. The IR and NMR spectra of this product were identical with those of the product obtained in Example 4. It was therefore determined to be 5-chloro-2'-fluoro-2-(2-methyl-5-phthalimidomethylpyrrol-1-yl)benzophenone.

EXAMPLE 18 [Preparation of compound (I)]

A mixture of 1.38 g (3.04 millimoles) of 5-chloro-2-(2-methyl-5-phthalimidomethylpyrrol-1-yl)benzophenone and 0.26 ml of hydrazine hydrate in 25 ml of ethanol was heated under reflux for 1.5 hours. The mixture was allowed to stand overnight at room temperature. The precipitated solid was separated by filtration. The filtrate was concentrated at reduced pressure to a volume of about 8 ml, and 25 ml of benzene was added. The mixture was washed with water and then with an aqueous solution of sodium chloride, dried over anhydrous sodium sulfate, and concentrated under reduced pressure. The residue was chromatographed on silica gel with benzene-ethyl acetate (19:1) as an eluant to afford 602 mg of light yellow crystals in a yield of 65%. Recrystallization from diethyl ether-n-hexane afforded light yellow prisms having a melting point of 144° to 145° C. The spectral data and the results of elemental analysis of the product were as follows:

IR (KBr) cm$^{-1}$: 1607, 1480, 1444, 1410, 1299, 998, 806, 776, 760, 692.

NMR (CDCl$_3$) from TMS, $\delta$ (ppm):
2.33 (3H, s, CH$_3$) $\nu_A$ 4.97 and $\nu_B$ 3.95 (2H, ABq, J=12.5 Hz, CH$_2$N) 7.02 (2H, m, $\omega$1/2=2 Hz, H on the pyrrole ring) 7.18–7.60 (8H, m, H on the benzene rings)

Analysis Calcd. for C$_{19}$H$_{15}$ClN$_2$: C, 74.39; H, 4.93; N, 9.13; Found: C, 74.29; H, 4.76; N, 9.06.

From the above characteristics, the product was determined to be 8-chloro-1-methyl-6-phenyl-4H-pyrrolo[1,2-a][1,4]benzodiazepine.

EXAMPLE 19 [Preparation of compound (I)]

2-Amino-5-chlorobenzophenone (860 mg, 3.72 millimoles) and 1-phthalimidohexane-2,5-dione (1.00 g, 3.86 millimoles) were dissolved in 20 ml of ethanol, and 620 mg of trichloroacetic acid was added. The mixture was heated under reflux for 2 hours, and then 0.7 ml of hydrazine hydrate was added, followed by heating under reflux for 1 hour. After cooling, 150 ml of water was added to the reaction mixture. It was extracted with benzene. The combined extracts were washed with an aqueous solution of sodium chloride, dried over anhydrous sodium sulfate, and concentrated under reduced pressure. The residue was chromatographed on silica gel with benzene-ethyl acetate (19:1) as an eluant to afford light yellow crystals. Recrystallization from diethyl ether-n-hexane afforded light yellow prisms having a melting point of 144° to 145° C. The product showed the same spectral data as the compound produced in Example 18 did, and was determined to be 8-chloro-1-methyl-6-phenyl-4H-pyrrolo[1,2-a][1,4] benzodiazepine.

EXAMPLE 20 [Preparation of compound (I)]

2-(2-Methyl-5-phthalimidomethylpyrrol-1-yl) benzophenone (570 mg, 1.36 millimoles) was dissolved in 15 ml of ethanol, and 0.2 ml of hydrazine hydrate was added. The mixture was heated under reflux for 1 hour, and cooled with an ice bath. The solid precipitated was separated by filtration, and the filtrate concentrated at reduced pressure. The concentrate was dissolved in 30 ml of benzene, washed with an aqueous solution of sodium chloride, dried over anhydrous sodium sulfate, and concentrated under reduced pressure. The concentrate was chromatographed on silica gel with benzene-ethyl acetate (19:1) as an eluant to afford 252 mg of light yellow crystals having a melting point of 141° to 143° C. in a yield of 68%. Recrystallization from diethyl ether-n-hexane afforded light yellow prisms having a melting point of 142.5° to 143.5° C. The spectral data and the results of elemental analysis of the product were as follows:

IR (KBr) cm$^{-1}$: 1610, 1485, 1442, 1400, 1325, 1312, 987, 761, 691.

NMR (CDCl$_3$) from TMS, $\delta$ (ppm): 2.35 (3H, s, CH$_3$) $\nu_A$ 4.95 and $\nu_B$ 3.96 (2H, ABq, J=12.5 Hz, CH$_2$N) 6.03 (2H, m, H on the pyrrole ring) 7.13–7.69 (9H, m, H on the benzene rings)

Analysis Calcd. for C$_{19}$H$_{16}$N$_2$: C, 83.79; H, 5.92; N, 10.29; Found: C, 83.72; H, 5.78; N, 10.28.

From the above characteristics, the product was determined to be 1-methyl-6-phenyl-4H-pyrrolo[1,2-a][1,4]benzodiazepine.

EXAMPLE 21 [Preparation of compound (I)]

A mixture of 300 mg (0.713 millimole) of 2-(2-methyl-5-phthalimidomethylpyrrol-1-yl)benzophenone and 536 mg (7.13 millimoles) of 2-methoxyethylamine in 2 ml of ethanol was heated under reflux for 30 minutes. The reaction mixture was concentrated at reduced pressure. The concentrate was taken in 5 ml of benzene and heated under reflux for 5 minutes. The reaction mixture was cooled, and the solid precipitated was separated by filtration. The filtrate was concentrated at reduced pressure, and the concentrate was chromatographed on silica gel with benzene as an eluant to afford 179 mg of colorless crystals having a melting point of 143° to 144° C. in a yield of 92%. This product showed the same IR and NMR spectra as 1-methyl-6-phenyl-4H-pyrrolo[1,2-a][1,4]benzodiazepine obtained in Example 20 did.

EXAMPLE 22 [Preparation of compound (I)]

2',5-Dichloro-2-(2-methyl-5-phthalimidomethylpyrrol-1-yl)benzophenone (869 mg, 1.78 millimoles) was dissolved in 20 ml of ethanol by heating and 0.3 ml of hydrazine hydrate was added. The mixture was heated under reflux for 1.5 hours. The reaction mixture was cooled with an ice-water bath, and the precipitated white solid was separated by filtration. The layers were separated, and the benzene layer was washed with an aqueous solution of sodium chloride, and dried over anhydrous sodium sulfate. The solvent was evaporated at reduced pressure, and the concentrate was chromatographed on silica gel with benzene-ethyl acetate (19:1) as an eluant to afford 528 mg of light yellow crystals in a yield of 87%. Recrystallization from methylene chloride-n-hexane afforded light yellow prisms having a melting point of 134° to 135.5° C. The spectral data and the results of elemental analysis of the products were as follows:

IR (KBr) cm$^{-1}$: 1605, 1481, 1411, 1323, 1313, 998, 754.

NMR (CDCl$_3$), $\delta$ (ppm) from TMS: 2.31 (3H, s, CH$_3$) $\nu_A$ 4.99 and $\nu_B$ 4.03 (2H, ABq, J=12.5 Hz, CH$_2$N) 6.04(2H, s, H on the pyrrole ring) 7.04 (1H, m, H on the benzene ring) 7.21–7.61 (6H, m, H on the benzene rings)

Analysis Calcd. for C$_{19}$H$_{14}$Cl$_2$N$_2$: C, 66.88; H, 4.14; N, 8.21; Found: C, 66.59; H, 4.04; N, 8.00.

From the above characteristics, the product was determined to be 8-chloro-6-(2-chlorophenyl)-1-methyl-4H-pyrrolo[1,2-a][1,4]benzodiazepine.

EXAMPLE 23 [Preparation of compound (I)]

5-Chloro-2'-fluoro-2-(2-methyl-5-phthalimidomethyl-pyrrol-1-yl)benzophenone (1.36 g, 2.88 millimoles) was dissolved in 20 ml of ethanol, and 0.3 ml of hydrazine hydrate was added. The mixture was heated under reflux for 3 hours. The reaction mixture was post-treated in the same manner as in Example 20, and chromatographed on silica gel with benzene as an eluant to afford 497 mg of light yellow crystals in a yield of 54%. Recrystallization from diethyl ether-in-hexane afforded light yellow prisms having a melting point of 99.5° to 100.5° C. The spectral data of the product were as follows:

IR (KBr) cm$^{-1}$: 1610, 1481, 1447, 1410, 1311, 1209, 822, 765, 755.

NMR (CDCl$_3$), δ (ppm) from TMS: 2.33 (3H, s, CH$_3$) $v_A$ 5.01 and $v_B$ 3.99 (2H, ABq, J=12.5 Hz, CH$_2$N) 2.33 (3H, s, CH$_3$) 6.05 (2H, s, H on the pyrrole ring) 6.86–7.69 (7H, m, H on the benzene rings)

Mass [70 eV, m/e (relative intensity)]: 326 (7%) and 324 (21%) (M+), 314 (34% and 309 (100%) (M-CH$_3$).

From the above characteristics, the product was determined to be 8-chloro-6-(2-fluorophenyl)-1-methyl-4H-pyrrolo[1,2-a][1,4]benzodiazepine.

77 mg of this product was dissolved in 10 ml of benzene, and under cooling, hydrogen chloride gas was introduced, whereupon yellow crystals precipitated. After standing for 30 minutes, the solvent was evaporated at reduced pressure. The residue was recrystallized from methanol-acetone to afford 63 mg of 8-chloro-6-(2-fluorophenyl)-1-methyl-4H-pyrrolo[1,2-a][1,4]benzodiazepine hydrochloride as yellow prisms having a melting point of 140° to 156° C. The IR spectral data of this product were as follows:

IR (KBr) cm$^{-1}$: 2550, 1634, 1608, 1577, 1549, 1477, 1440, 1386, 1328.

EXAMPLE 24 [Preparation of compound (I)]:

A mixture of 100 mg (0.22 millimole) of 2-(2-methyl-5-phthalimidomethylpyrrol-1-yl)-5-nitrobenzophenone, 0.05 ml of hydrazine hydrate, 1, ml of N,N-dimethyl formamide and 3 ml of ethanol was heated under reflux for 30 minutes, and cooled with an ice bath. The resulting white solid was separated by filtration. The filtrate was treated in the same manner as in Example 20, and chromatographed on silica gel with benzene-ethyl acetate (96:4) as an eluant. Fractions containing the desired product were collected, and the solvent was evaporated. Then, a small amount of diethyl ether was added to the residue. The ether-soluble portion was removed, and 48 mg of yellow crystals were obtained in a yield of 71%. Recrystallization from methylene chloride-n-hexane afforded yellow prisms having a melting point of 200° to 201.5° C. The spectral data and the results of elemental analysis were as follows:

IR (KBr) cm$^{-1}$: 1610, 1515, 1480, 1341, 1335 (shoulder), 1315 (shoulder), 778, 766, 689.

NMR (CDCl$_3$), δ (ppm) from TMS: 2.39 (3H, s, CH$_3$) $v_A$ 5.06 and $v_B$ 3.98 (2H, ABq, J=12.5 Hz, CH$_2$N) 6.11 (2H, s, H on the pyrrole ring) 7.24–7.65 (6H, m, H on the benzene rings) 8.22–8.46 (2H, m, H on the benzene rings)

Analysis: Calcd. for C$_{19}$H$_{15}$N$_3$O$_2$: C, 71.91; H, 4.76; N, 13.24: Found: C, 71.65; H, 4.67; N, 12.89.

From the above characteristics, this product was determined to be 1-methyl-8-nitro-6-phenyl-4H-pyrrolo[1,2-a][1,4]benzodiazepine.

EXAMPLE 25 [Preparation of compound (I)]

5-Chloro-2-(2,3-dimethyl-5-phthalimidomethylpyrrol-1-yl)benzophenone (322 mg, 0.687 millimole) was dissolved in a mixture of 5 ml of ethanol and 1 ml of N,N-dimethylforamide, and 0.2 ml of hydrazine hydrate (100%) was added. The mixture was heated at 100° C. for 50 minutes, and cooled. The resulting white solid was separated by filtration. To the filtrate were added 80 ml of benzene and 50 ml of water, and the layers were separated. The benzene layer was washed with a saturated aqueous solution of sodium chloride, and dried over anhydrous sodium sulfate. The solvent was evaporated, and the residue was chromatographed on silica gel with benzene-ethyl acetate (19:1) as an eluant to afford 124 mg of yellow crystals having a melting point of 189° to 191.5° C. in a yield of 56%. Recrystallization from methylene chloride-n-hexane afforded light yellow prisms having a melting point of 190.5° to 191.5° C. The spectral data and the results of elemental analysis of the product were as follows:

IR (KBr) cm$^{-1}$: 1610, 1573, 1483, 1447, 1406, 1353, 1313.

NMR (CDCl$_3$), δ (ppm): 2.02 (3H, s, CH$_3$ at the 2-position) 2.23 (3H, s, CH$_3$ at the 1-position) $v_A$ 4.95 and $v_B$ 3.94 (2H, ABq, J=11.0 Hz, CH$_2$N) 5.96 (1H, s, H on the pyrrole ring) 7.23–7.59 (8H, m, H on the benzene rings)

Analysis Calcd. for C$_{20}$H$_{17}$ClN$_2$: C, 74.88; H, 5.34; N, 8.73; Found: C, 74.60; H, 5.43; N, 8.52.

From the above characteristics, the product was determined to be 8-chloro-1,2-dimethyl-6-phenyl-4H-pyrrolo[1,2-a][1,4]benzodiazepine.

EXAMPLE 26 [Preparation of compound (I)]

2′,5-Dichloro-2-(2,3-dimethyl-5-phthalimidomethyl-pyrrol-1-yl)benzophenone (504 mg, 1.00 millimole) was dissolved in a mixture of 8 ml of ethanol and 2 ml of N,N-dimethylformamide, and 0.2 ml of hydrazine hydrate was added. The mixture was heated at 100° C. for 30 minutes. The reaction mixture was post-treated in the same way as in Example 25, and then chromatographed on silica gel. The column was first eluted with benzene and then with a mixture of benzene and ethyl acetate (9:1) to afford 320 mg of yellow crystals having a melting point of 131° to 133° C. in a yield of 90%. Recrystallization from diethyl ether-n-hexane afforded light yellow prisms having a melting point of 132.5° to 133.5° C. The spectral data of this product were as follows:

IR (KBr) cm$^{-1}$: 1607, 1482, 1407, 1311, 828, 763, 748.

NMR (CDCl$_3$), δ (ppm) from TMS: 2.05 (3H, s, CH$_3$ at the 2-position) 2.21 (3H, s, CH$_3$ at the 1-position) $v_A$ 4.98 and $v_B$ 4.00 (2H, ABq, J=12.5 Hz, CH$_2$N) 5.97 (1H, s, H on the pyrrole ring) 7.04 (1H, m, H on the benzene ring) 7.10–7.60 (6H, m, H on the benzene rings)

Mass [70 eV, m/e (relative intensity)]358 (3%), 356 (12%) and 354 (19%) (M+); 343 (12%), 341 (66%), and 339 (100%) (M—CH$_3$).

From the above characteristics, the product was determined to be 8-chloro-6-(2-chlorophenyl)-1,2-dimethyl-4H-pyrrolo[1,2-a][1,4]benzodiazepine.

50 mg of this product was dissolved in 6 ml of dry benzene, and hydrogen chloride was was introduced for 10 minutes. After standing overnight at room temperature, the resulting crystals were collected by filtration. Recrystallization from methanol-benzene afforded the hydrochloride of the above diazepine as prisms having a melting point of 143° to 147° C. The IR spectral data of the ydrochloride were as follows:

IR (KBr) cm$^{-1}$: 3180, 2550, 2100, 1641, 1585, 1479, 1405, 1356, 1343, 768, 754.

EXAMPLE 27 [Preparation of compound (I)]

5-Chloro-2-(2,3-dimethyl-5-phthalimidomethylpyrrol-1-yl)-2′-fluorobenzophenone (400 mg, 0.821 millimole) was dissolved in a mixture of 6 ml of ethanol and 1 ml of N,N-dimethylformamide, and 0.2 ml of hydrazine hydrate was added. The mixture was heated at 100° C. for 20 minutes. The reaction mixture was post-treated and chromatographed on silica gel in the same manner as in Example 25 to afford 190 mg of yellow crystals having a melting point of 181° to 183° C. in a yield of 68%. Recrystallization from methylene chloride-n-hexane afforded light yellow prisms having a melting point of 182.5° to 183.5° C. The spectral data and the results of elemental analysis of the product were as follows:

IR (KBr) cm$^{-1}$: 1609, 1481, 1450, 1409, 1315, 1205, 830, 749.

NMR (CDCl$_3$), δ (ppm) from TMS: 2.04 (3H, s, CH$_3$ at the 2-position) 2.23 (3H, s, CH$_3$ at the 1-position) ν$_A$ 4.98 and ν$_B$ 3.96 (2H, ABq, J=13.0 Hz, CH$_2$N) 5.96 (1H, s, H on the pyrrole ring) 8.86–7.68 (7H, m, H on the benzene rings)

Mass [70 eV, m/e (relative intensity)]340 (7%) and 338 (20%) (M+), 325 (36%) and 323 (100%) (M-CH$_3$)

Analysis Calcd. for C$_{20}$H$_{16}$ClFN$_2$: C, 70.90; H, 4.76; N, 8.27; Found: C, 70.76; H, 5.17; N, 8.15.

From the above characteristics, the product was determined to be 8-chloro-1,2-dimethyl-6-(2-fluorophenyl)-4H-pyrrolo[1,2-a][1,4]benzodiazepine.

EXAMPLE 28 [Preparation of compound (I)]

A mixture of 499 mg (0.964 millimole) of 2',5-dichloro-2-(3-ethyl-2-methyl-5-phthalimidomethylpyrrol-1-yl)benzophenone, 0.4 ml of hydrazine hydrate (100%), 4 ml of N,N-dimethylformamide and 10 ml of ethanol was heated under reflux for 1 hour, and the reaction mixture was concentrated at reduced pressure. A white solid formed. 20 ml of benzene was added, and the mixture was cooled. The solid was separated by filtration. The filtrate was washed with water and then with an aqueous solution of sodium chloride, dried over anhydrous sodium sulfate, and concentrated under reduced pressure. The residue was chromatographed on silica gel with benzene-ethyl acetate (96:4) as an eluant to afford 293 mg of light yellow crystals in a yield of 82%. Recrystallization from diethyl ether-n-hexane afforded light yellow prisms having a melting point of 136.5° to 137.5° C. The spectral data and the results of elemental analysis of the product were as follows:

IR (KBr) cm$^{-1}$: 1606, 1482, 1407, 1311, 820, 764, 748.

NMR (CDCl$_3$), δ (ppm) from TMS: 1.18 (3H, t, J=7.5 Hz, CH$_2$CH$_3$) 2.12 (3H, s, =C—CH$_3$) 2.45 (2H, q, J=7.5 Hz, CH$_2$CH$_3$) ν$_A$ 4.99 and ν$_B$ 4.02 (2H, ABq, J=12.5 Hz, CH$_2$N) 6.03 (1H, d, J=2.0 Hz, H on the benzene ring) 7.23–7.60 (6H, m, H on the benzene rings)

Analysis Calcd. for C$_{21}$H$_{18}$Cl$_2$N$_2$: C, 68.30; H, 4.91; N, 7.59; Found: C, 68.14; H, 4.68, N, 7.72.

From the above characteristics, the product was determined to be 8-chloro-6-(2-chlorophenyl)-2-ethyl-1-methyl-4H-pyrrolo[1,2-a][1,4]benzodiazepine.

EXAMPLE 29 [Preparation of compound (I)]

A mixture of 454 mg (0.906 millimole) of 5-chloro-2-(3-ethyl-2-methyl-5-phthalimidomethylpyrrol-1-yl)-2'-fluorobenzophenone, 0.4 ml of hydrazine hydrate (100%), 4 ml of N,N-dimethylformamide and 4 ml of ethanol was heated under reflux for 1 hour. The reaction mixture was concentrated under reduced pressure. The reaction mixture was treated in the same manner as in Example 28, and chromatographed on silica gel. The column was first eluted with benzene, and then with benzene-ethyl acetate (19:1) to afford 174 mg of light yellow crystals in a yield of 54%. Recrystallization from diethyl ether-n-hexane afforded light yellow prisms having a melting point of 169° to 170° C. The spectral data and the results of elemental analysis of the product were as follows:

IR (KBr) cm$^{-1}$: 1608, 1480, 1450, 1408, 1315, 1208, 830, 763, 749.

NMR (CDCl$_3$), δ (ppm) from TMS: 1.17 3H, t, J=7.5 Hz, CH$_2$CH$_3$) 2.23 (3H, s, =C—CH$_3$) 2.43 (2H, q, J=7.5 Hz, CH$_2$CH$_3$) ν$_A$ 4.99 and ν$_B$ 3.97 (2H, ABq, J=12.5 Hz, CH$_2$N) 6.00 (1H, s, H on the pyrrole ring) 6.86–7.68 (7H, m, H on the benzene rings)

Analysis Calcd. for C$_{21}$H$_{18}$ClFN$_2$: C, 71.49; H, 5.14; N, 7.94 Found: C, 71.44; H, 5.16; N, 7.84

From the above characteristics, the product was determined to be 8-chloro-2-ethyl-6-(2-fluorophenyl)-1-methyl-4H-pyrrolo[1,2-a][1,4]benzodiazepine.

EXAMPLE 30 [Preparation of compound of formula (I)]

2-Aminot-2',5-dichlorobenzophenone (285 mg, 1.07 millimoles) and 4-methyl-1-phthalimidohexane-2,5-dione (300 mg, 1.10 millimoles) were dissolved in 5 ml of ethanol, and 30 mg of p-toluenesulfonic acid was added. The mixture was heated under reflux for 1 hour, and 0.3 ml of hydrazine hydrate (100%) and 1 ml of N,N-dimethylformamide were added. The mixture was further heated under reflux for 15 minutes. The reaction mixture was post-treated in the same way as in Example 28, and then chromatographed on silica gel in the same way as in Example 29 to afford yellow crystals. Recrystallization from diethyl ether-n-hexane afforded light yellow crystals having a melting point of 132.5° to 133.5° C. which showed the same IR and NMR spectra as those of 8-chloro-6-(2-chlorophenyl)-1,2-dimethyl-4H-pyrrolo[1,2-a][1,4]bezodiazepine obtained in Example 26.

EXAMPLE 31 [Preparation of compound (I)]

5-Chloro-2',6'-difluoro-2-(3-ethyl-2-methyl-5-phthalimidomethylpyrrol-1-yl)benzophenone (578 mg, 1.11 millimoles) was dissolved in 4 ml of N,N-dimethylformamide by heating, and 10 ml of ethanol and 0.2 ml of hydrazine hydrate (100%) were added, and the mixture was heated in an oil bath at 100° C. for 1 hour. The ethanol was evaporated under reduced pressure, and 30 ml of benzene was added to the residue. The mixture was heated under reflux for 5 minutes. The reaction mixture was cooled, and the resulting white crystals were separated by filtration. The filtrate was washed with water and an aqueous solution of sodium chloride, dried over anhydrous sodium sulfate, and concentrated under reduced pressure. The concentrate was chromatographed on silica gel with benzene-ethyl acetate (24:1) as an eluant to afford 358 mg of yellow crystals having a melting point of 202° to 203.5° C. in a yield of 87%. Recrystallization from methylene chloride-n-hexane afforded light yellow prisms having a melting point of 204.5° to 205° C. The spectral data and the results of elemental analysis of the product were as follows:

IR (KBr) cm$^{-1}$: 1616, 1482, 1462, 1410, 1307, 1233, 1016, 982, 825, 786.

NMR (CDCl$_3$), δ (ppm) from TMS: 1.17 (3H, t J=7.5 Hz, CH$_2$CH$_3$) 2.22 (3H, s, =C—CH$_3$) 2.44 (2H, q, J=7.5Hz, CH$_2$CH$_3$) ν$_A$ 5.04 and ν$_B$ 4.06 (2H, ABq, J=13.0 Hz) 6.03 (1H, s, H on the pyrrole ring) 6.79–6.96 (2H, m, H on the benzene rings) 7.16–7.49 (4H, m, H on the benzene rings)

Analysis Calcd. for C$_{21}$H$_{17}$ClF$_2$N$_2$: C, 68.02; H, 4.62; N, 7.55; Found: C, 67.98; H, 4.63; N, 7.36.

From the above characteristics, the above product was determined to be 8-chloro-2-ethyl-6-(2,6-difluorophenyl)-1-methyl-4H-pyrrolo[1,2-a][1,4]benzodiazepine.

EXAMPLE 32 [Preparation of compound (I)]

2',5-Dichloro-2-(2,4-dimethyl-5-phthalimidomethylpyrrol-1-yl)benzophenone (608 mg, 1.21 millimoles) was dissolved in 2 ml of N,N-dimethylformamide by heating and 8 ml of ethanol and 0.2 ml of hydrazine hydrate were added. The mixture was heated under reflux for 30 minutes. The reaction mixture was post-treated in the same way as in Example 33, and chromatographed on silica gel with benzene-ethyl acetate (49:1) as an eluant to afford 368 mg of yellow crystals having a melting point of 130.5° to 132° C. in a yield of 86%. Recrystallization from diethyl ether-n-hexane afforded light yellow prisms having a melting point of 132° to 133° C. The spectral data and the results of elemental analysis of the product were as follows:

IR (KBr) cm$^{-1}$: 1616, 1481, 1414, 1362, 1314, 811, 761.

NMR (CDCl$_3$), δ (ppm) from TMS: 2.10 (H, s, CH$_3$ at the 3-position) 2.28 (3H, s, CH$_3$ at the 1-position) $v_A$ 5.07 and $v_B$ 3.94 (2H, ABq, J=13.0 Hz. CH$_2$N) 5.97 (1H, s, H on the pyrrole ring) 7.06 (1H m, H on the benzene ring) 7.23–7.62 (6H, m, H on the benzene rings)

Analysis Calcd. for C$_{20}$H$_{16}$Cl$_2$N$_2$: C, 67.62; H, 4.54; N, 7.89; Found: C, 67.58; H, 4.33; N, 7.64.

From the above characteristics, the product was determined to be 8-chloro-6-(2-chlorophenyl=-1,3-dimethyl-4H-pyrrolo[1,2-a][1,4]benzodiazepine.

41 mg of this product was dissolved in 8 ml of dry benzene, and hydrogen chloride gas was introduced to the solution. After standing overnight at room temperature, the solvent was evaporated under reduced pressure. A small amount of diethyl ether was added to the residue, and the mixture was filtered to afford 37 mg of 8-chloro-6-(2-chlorophenyl)-1,3-dimethyl-4H-pyrrolo[1,2-a][1,4]benzodiazepine hydrochloride as light red crystals having a melting point of 145° to 154° C. The IR spectral data of the hydrochloride were as follows:

IR (KBr) cm$^{-1}$: 3140, 2520 (broad), 1638, 1613, 1583, 1481, 1410, 1331, 771.

EXAMPLE 33 [Preparation of compound (I)]

5-Chloro-2'-fluoro-2-(2,4-dimethyl-5-phthalimidomethylpyrrol-1-yl)benzophenone (507 mg, 1.04 millimoles) was dissolved in 3 ml of N,N-dimethylformamide by heating and 10 ml of ethanol and 0.3 ml of hydrazine hydrate (100%) were added. The mixture was heated under reflux for 1.5 hours. The reaction mixture was post-treated in the same manner as in Example 31, and then chromatographed on silica gel with benzene-ethyl acetate (19:1) as an eluant to afford 170 mg of yellow crystals in a yield of 48%. Recrystallization from diethy ether-n-hexane afforded light yellow prisms having a melting point of 99.5° to 101° C. The spectral data and the results of elemental analysis of the product were as follows:

IR (KBr) cm$^{-1}$: 1612, 1482, 1449, 1413, 1211, 826, 766, 752.

NMR (CDCl$_3$), δ (ppm) from TMS: 2.11 (3H, s, CH$_3$ at the 3-position) 2.30 (3H, s, CH$_3$ at the 1-position) $v_A$ 4.07 and $v_B$ 3.93 (2H, ABq, J=12.5 Hz, CH$_2$N) 5.96 (1H, s, H on the pyrrole ring) 6.78–7.72 (7H, m, H on the benzene rings)

Analysis Calcd. for C$_{20}$H$_{16}$ClFN$_2$: C, 70.90; H, 4.76; N, 8.27; Found: C, 70.92; H, 4.91; N, 8.07.

From the above characteristics, the product was determined to be 8-chloro-1,3-dimethyl-6-(2-fluorophenyl)-4H-pyrrolo[1,2-a][1,4]benzodiazepine.

EXAMPLE 34 [Preparation of compound (I)]

5-Chloro-2',6'-difluoro-2-(2,4-dimethyl-5-phthalimidomethylpyrrol-1-yl)benzophenone (541 mg, 1.07 millimoles) was dissolved in 2 ml of N,N-dimethylformamide by heating, and 10 ml of ethanol and 0.2 ml of hydrazine hydrate (100%) were added. The mixture was heated under reflux for 50 minutes. The reaction mixture was post-treated and chromatographed on silica gel in the same way as in Example 33 to afford 318 mg of a light brown glassy substance in a yield of 83%. The spectral data of the substance were as follows:

IR (KBr) cm$^{-1}$: 1621, 1481, 1461, 1412, 1232, 1012, 987, 787.

NMR (CDCl$_3$), δ (ppm) from TMS: 2.11 (3H, s, CH$_3$ at the 3-position) 2.29 (3H, s, CH$_3$ at the 1-position) $v_A$ 5.13 and $v_B$ 4.00 (2H, ABq, J=12.5 Hz, CH$_2$N) 5.99 (1H, s, H on the pyrrole ring) 6.81–7.55 (6H, m, H on the benzene rings)

From the above characteristics, the product was determined to be 8-chloro-6-(2,6-difluorophenyl)-1,3-dimethyl-4H-pyrrolo[1,2-a][1,4]benzodiazepine.

EXAMPLE 35 [Preparation of compound (I)]

2-Amino-2',5-dichlorobenzophenone (200 mg, 0.752 millimole) and 3-methyl-1-phthalimidohexane-2,5-dione (225 mg, 0.823 millimole) were dissolved in 10 ml of benzene, and 20 mg of p-toluenesulfonic acid was added. The mixture was heated under reflux for 4 hours, and 2 ml of N,N-dimethylformamide was added. The benzene was evaporated under reduced pressure, and 8 ml of ethanol and 0.3 ml of hydrazine hydrate were added. The mixture was heated under reflux for 30 minutes. The ethanol was evaporated under reduced pressure, and 25 ml of benzene was added. The mixture was heated under reflux for 5 minutes. After cooling, the solid was separated by filtration. The filtrate was washed with water and an aqueous solution of sodium chloride, and dried over anhydrous sodium sulfate. The solvent was evaporated under reduced pressure, and the concentrate was chromatographed on silica gel. The column was first eluted with benzene to recover unchanged 2-amino-2',5-dichlorobenzophenone, and then with benzene-ethyl acetate (49:1) to afford 145 mg of 8-chloro-6-(2-chlorophenyl)-1,3-dimethyl-4H-pyrrolo[1,2-a][1,4]benzodiazepine as yellow crystals in a yield of 54%. The product showed the same spectral data as those of the compound obtained in Example 32.

Referential Example 1 [Preparation of compound (IV)]

3-Methyl-1-phthalimidohex-3-ene-2,5-dione (423 mg, 1.56 millimoles) was catalytically hydrogenated with 300 mg of Raney nickel (containing ethanol) in 45 ml ethyl acetate using a catalytic reduction apparatus. In 12 minutes, hydrogen was absorbed in an amount stoichiometrically required to hydrogenate the carbon-carbon double bond of the above compound. The catalyst was separated by suction filtration with a care taken not to bring it into contact with the air. The solvent was evaporated from the filtrate under reduced pressure to afford 416 mg of 3-methyl-1-phthalimidohexane-2,5-dione as white crystals in a yield of 98%. Recrystallization from methanol afforded colorless prisms having a melting point of 101.5° to 102.5° C. The spectral data and the results of elemental analysis of the product were as follows:

IR (KBr) cm$^{-1}$: 1765, 1720, 1703 (shoulder), 1413, 1396, 1375, 1058, 720, 711.

NMR (CDCl$_3$), δ (ppm) from TMS: 1.22 (3H, d, J=7.0 Hz, CH$_3$) 2.21 (3H, s, —CO—CH$_3$) 2.40–3.36 (3H, m, C—CH$_2$CO and CH$_3$CHCO) $\nu_A$ 4.70 and $\nu_B$ 4.60 (2H, ABq, J=18.0 Hz, CH$_2$N) 7.61–7.95 (4H, m, H on the benzene ring)

Analysis Calcd. for C$_{15}$H$_{15}$NO$_4$: C, 65.93; H, 5.53; N, 5.13 Found: C, 65.68; H, 5.45; N, 5.24

Referential Example 2 [Preparation of compound (V)]

Using 5 ml of suspension of Raney nickel in ethanol, 2.00 g (6.59 millimoles) of 2,5-dimethoxy-2-methyl-5-phthalimidomethyldihydrofuran was hydrogenated in 20 ml of ethyl acetate. In 15 minutes at room temperature, hydrogen was absorbed in a stoichiometrical amount. The catalyst was separated by filtration, and the solvent in the filtrate was evaporated under reduced pressure to afford 1.93 g of 2,5-dimethoxy-2-methyl-5-phthalimidomethyltetrahydrofuran as colorless crystals in a yield of 96%. Recrystallization from ethyl ether-n-hexane afforded colorless prisms having a melting point of 113.5° to 114.5° C. The spectral data and the results of elemental analysis of the product were as follows:

IR (KBr) cm$^{-1}$: 1767, 1710, 1421, 1389, 1331, 1242, 1122, 1087, 1018, 879, 728.

NMR (CDCl$_3$), δ (ppm) from TMS: 1.47 (3H, s, CH$_3$) 1.77–2.56 (4H, m, CH$_2$CH$_2$) 3.16 (3H, s, OCH$_3$) 3.33 (3H, s, OCH$_3$) $\nu_A$ 4.06 and $\nu_B$ 3.84 (2H, ABq, J=14.0 Hz, CH$_2$N) 7.60–7.91 (4H, m, H on the benzene ring)

Analysis Calcd. for C$_{16}$H$_{19}$NO$_5$: C, 62.94; H, 6.27; N, 4.59; Found: C, 62.88; H, 6.29; N, 4.74.

Formulation Example 1 (tablets)

| | |
|---|---|
| 8-Chloro-6-(2,difluorophenyl)-1,3-dimethyl-4H-pyrrolo(1,2-a)(1,4)-benzodiazepine | 10.0 mg |
| Lactose | 113.5 mg |
| Potato starch | 70.5 mg |
| Calcium stearate | 3.0 mg |
| | 197.0 mg/tablet |

The active compound was pulverized by a pulverizer, and the particles which passed through a 100-mesh screen were collected. These particles were mixed with the lactose and potato starch in a mixer, and then kneaded in a kneader using 3% starch paste. The kneaded mixture was passed through a granulator to form granules. The granules were dried by a hot air dryer at 60° C. After drying, the size was adjusted by passing the granules through a 20-mesh screen and the granules lightly mixed with calcium stearate in a mixer. The mixture was compressed to form tablets each having a weight of about 200 mg.

Formulation Example 2 (tablets)

| | |
|---|---|
| 8-Chloro-6-(2-fluorophenyl)-1,2-dimethyl-4H-pyrrolo(1,2-a)(1,4)benzodiazepine | 25 mg |
| Lactose | 355 mg |
| Microcrystalline cellulose | 100 mg |
| Starch | 16 mg |
| Calcium stearate powder | 4 mg |
| | 500 mg/tablet |

The active compound (passed through 100-mesh screen) was mixed well with the rest of the ingredients, and the mixture was compressed to form tablets each having a weight of 500 mg.

Formulation Example 3 (capsules)

| | |
|---|---|
| 8-Chloro-6-(2-chlorophenyl)-2-ethyl-1-methyl-4H-pyrrolo-(1,2-a)(1,4)benzodiazepine | 10 mg |
| Lactose | 158 mg |
| Corn starch | 37 mg |
| Talc | 3 mg |
| | 208 mg/capsule |

The active compound (passed through 100-mesh screen) was mixed well with the lactose and corn starch in a mixer. Talc was lightly mixed with the resulting mixture. The mixture was filled in hard gelatin capsules using a capsule-packing machine.

Formulation Example 4 (capsules)

In the same way as in Formulation Example 4, capsules of the following composition were obtained.

| | |
|---|---|
| 8-Chloro-6-(2-chlorophenyl)-1,3-dimethyl-4H-pyrrolo(1,2-a)(1,4)benzodiazepine | 1.0 mg |
| Talc | 2.5 mg |
| Lactose | 125.0 mg |
| Magnesium stearate | 2.5 mg |
| Starch | 30.0 mg |
| | 161 mg/capsule |

Formulation Example 5 (injection)

| | |
|---|---|
| 8-Chloro-6-(2-chlorophenyl)-2-ethyl-1-methyl-4H-pyrrolo(1,2-a)(1,4)benzodiazepine | 10 g |
| Benzyl benzoate | 2 ml |
| Methyl p-hydroxybenzoate | 1.5 g |
| Propyl p-hydroxybenzoate | 0.5 g |

Cotton seed oil was added to the above composition to make the entire volume 1000 ml. The composition was then packed into 1-ml sterilized vials, followed by sealing.

Formulation Example 6 (injection)

Ten g of 8-chloro-6-(2-chlorophenyl)-1,2-dimethyl-4H-pyrrolo[1,2-a][1,4]benzodiazepine p-toluenesulfonate was dissolved in water for injection to make the entire volume 1000 ml. The solution was sterilized by filtration. The sterilized solution was packed into 1-ml sterilized ampoules.

Formulation Example 7 (suppository)

| | |
|---|---|
| 8-Chloro-6-(2-chlorophenyl)-1,3 dimethyl-4H-pyrrolo(1,2-a)(1,4)benzodiazepine | 2 mg |
| Polyethylene glycol 4000 | 1.24 g |
| Polyethylene glycol Polyoxyethylene | 0.23 g |

| | |
|---|---|
| Polyoxyl stearate | 0.20 g |
| Glycerine monostearate | 0.01 g |
| | 1.502 g/piece |

A base consisting of polyethylene glycol 4000, polyoxyethylene glycol 1500, polyoxyl stearate and glycerine monostearate was melted at about 70° C. The active compound shown above was added and dissolved with stirring. The molten liquid was poured into molds (1.5 ml/piece) for anus suppositories, and cooled and solidified to form suppositories (total weight 1.5 g; active ingredient 2 mg).

What is claimed is:

1. A compound of the formula

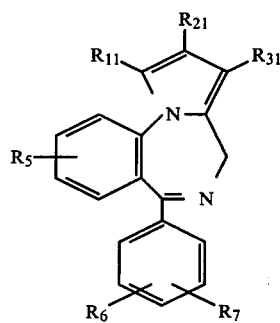

wherein $R_{11}$, $R_{21}$ and $R_{31}$ are identical to, or different from, each other, and at least one of them represents alkyl of 1 to 3 carbon atoms, and the remainder hydrogen; $R_5$ represents halogen, nitro or trifluoromethyl; and $R_6$ and $R_7$, independently from each other, represent hydrogen or halogen or an acid addition salt thereof.

2. A compound according to claim 1 wherein $R_{11}$, $R_{21}$ and $R_{31}$ are identical to, or different from, each other, and at least one of them represents methyl or ethyl, and the remainder hydrogen.

3. The compound of claim 1 which is 8-chloro-1-methyl-6-phenyl-4H-pyrrolo[1,2-a][1,4]benzodiazepine.

4. The compound of claim 1 which is 8-chloro-6-(2-chlorophenyl)-1-methyl-4H-pyrrolo[1,2-a][1,4]benzodiazepine.

5. The compound of claim 1 which is 8-chloro-6-(2-fluorophenyl)-1-methyl-4H-pyrrolo[1,2-a][1,4]benzodiazepine.

6. The compound of claim 1 which is 8-chloro-1,2-dimethyl-6-phenyl-4H-pyrrolo[1,2-a][1,4]benzodiazepine.

7. The compound of claim 1 which is 8-chloro-6-(2-chlorophenyl)-1,2-dimethyl-4H-pyrrolo[1,2-a][1,4]benzodiazepine.

8. The compound of claim 1 which is 8-chloro-1,2-dimethyl-6-(2-fluorophenyl)-4H-pyrrolo[1,2-a][1,4]-benzodiazepine 9. The compound of claim 1 which is 8-chloro-6-(2-chlorophenyl)-2-ethyl-1-methyl-4H-pyrrolo[1,2-a][1,4]-benzodiazepine.

10. The compound of claim 1 which is 8-chloro-2-ethyl-6-(2-fluorophenyl)-1-methyl-4H-pyrrolo[1,2-a][1,4]-benzodiazepine.

11. The compound of claim 1 which is 8-chloro-2-ethyl-6-(2,6-difluorophenyl)-1-methyl-4H-pyrrolo[1,2-a][1,4]benzodiazepine.

12. The compound of claim 1 which is 8-chloro-6-(2-chlorophenyl)-1,3-dimethyl-4H-pyrrolo[1,2-a][1,4]benzodiazepine.

13. The compound of claim 1 which is 8-chloro-1,3-dimethyl-6-(2-fluorophenyl)-4H-pyrrolo[1,2-a][1,4]benzodiazepine.

14. The compound of claim 1 which is 8-chloro-6-(2,6-difluorophenyl)-1,3-dimethyl-4H-pyrrolo[1,2-a][1,4]-benzodiazepine.

15. The compound of claim 1 which is 1-methyl-8-nitro-6-phenyl-4H-pyrrolo[1,2-a][1,4]benzodiazepine.

16. A pharmaceutical composition for prevention or treatment of diseases in a mammal or poultry accompanied by anxiety, excitation or convulsions comprising a pharmaceutically effective amount to prevent or treat such disease of at least one compound of the formula

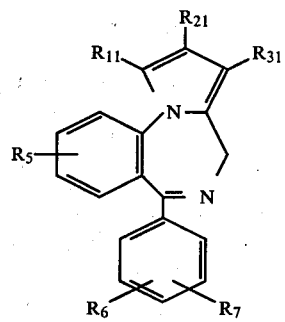

wherein $R_{11}$, $R_{21}$ and $R_{31}$ are identical to, or different from, each other, and at least one of them represents alkyl of 1 to 3 carbon atoms and the remainder hydrogen; $R_5$ represents halogen, nitro or trifluoromethyl; and $R_6$ and $R_7$, independently from each other represent hydrogen or halogen, or a pharmaceutically acceptable acid addition salt thereof, and a pharmaceutically acceptable carrier or diluent.

17. The pharmaceutical composition of claim 16 which is in an orally administrable form.

18. The pharmaceutical composition of claim 16 which is in a form suitable for subcutaneous, intramuscular, intravenous or intrarectal administration.

19. The pharmaceutical composition of claim 16 which is in the form of dosage unit.

20. The pharmaceutical composition of claim 16 which is in the form of a tablet, troche, pill, capsule, powder, granule, dry syrup, sugar-coated pill, syrup, elixir, suspension, suppository, or injectable.

21. A method for preventing or treating a mammal or poultry for a disease accompanied by anxiety, excitation or convulsion, which comprises administering to the mammal or poultry an effective amount to prevent or treat said disease, of a compound of the formula

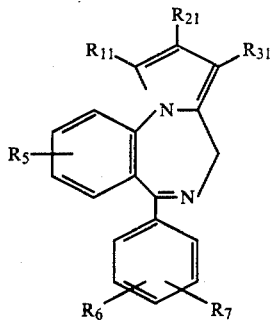

wherein $R_{11}$, $R_{21}$ and $R_{31}$ are identical to, or different from, each other, and at least one of them represents alkyl of 1 to 3 carbon atoms and the remainder hydrogen; $R_5$ represents halogen, nitro or trifluoromethyl; and $R_6$ and $R_7$ independently from each other represent hydrogen or halogen, or a pharmaceutically acceptable acid addition salt thereof.

22. The method of claim 21 wherein the mammal is a human being.

23. The method of claim 22 wherein the dosage of the compound is 0.03 to 3 mg/kg body weight/day.

24. The compound according to claim 1 in which said halogen is chlorine or fluorine.

25. The composition according to claim 16 in which said halogen is chlorine or fluorine.

26. The method according to claim 21 in which said halogen is chlorine or fluorine.

* * * * *